(12) United States Patent
Chatterjee et al.

(10) Patent No.: US 6,288,231 B1
(45) Date of Patent: Sep. 11, 2001

(54) PEPTIDE-CONTAINING α-KETOAMIDE CYSTEINE AND SERINE PROTEASE INHIBITORS

(75) Inventors: Sankar Chatterjee, Wynnewood; John P. Mallamo, Glenmoore; Ron Bihovsky, Wynnewood; Gregory J. Wells, West Chester, all of PA (US)

(73) Assignee: Cephalon, Inc., West Chester, PA (US)

( * ) Notice: Subject to any disclaimer, the term of this patent is extended or adjusted under 35 U.S.C. 154(b) by 0 days.

(21) Appl. No.: 09/527,540

(22) Filed: Mar. 16, 2000

Related U.S. Application Data

(62) Division of application No. 09/166,808, filed on Oct. 6, 1998.
(60) Provisional application No. 60/061,309, filed on Oct. 7, 1997.

(51) Int. Cl.⁷ ................ C07D 207/02; C07D 213/04; C07D 333/02; C07D 333/50; C07D 239/20
(52) U.S. Cl. ............... 544/316; 546/339; 546/329; 546/280.4; 549/29; 549/41; 564/102; 564/372; 530/300; 544/316; 548/240; 548/361
(58) Field of Search ............... 549/29, 41; 564/102, 564/372, 280.4; 546/329, 339; 530/300; 544/316, 240; 548/240, 361

(56) References Cited

U.S. PATENT DOCUMENTS

| | | | |
|---|---|---|---|
| 5,034,376 | 7/1991 | Hoover et al. | 514/18 |
| 5,162,500 | 11/1992 | Takeuchi et al. | 530/330 |
| 5,340,825 | 8/1994 | Horwell et al. | 514/339 |
| 5,444,042 | 8/1995 | Bartus et al. | 514/2 |
| 5,514,694 | 5/1996 | Powers et al. | 514/357 |
| 5,563,127 | 10/1996 | Amparo et al. | 514/64 |
| 5,610,297 | * 3/1997 | Powers | 544/168 |
| 5,614,649 | 3/1997 | Iqbal et al. | 554/56 |
| 5,646,121 | 7/1997 | Häbich et al. | 514/18 |
| 5,650,508 | * 7/1997 | Powers | 544/168 |
| 5,658,885 | 8/1997 | Lee et al. | 514/19 |
| 5,698,538 | 12/1997 | Amparo et al. | 514/64 |
| 5,763,576 | * 6/1998 | Powers | 530/330 |

FOREIGN PATENT DOCUMENTS

| | | |
|---|---|---|
| 0 604 183 A1 | 6/1994 | (EP) . |
| WO 95/00535 | 1/1995 | (WO) . |
| WO 96/14857 | 5/1996 | (WO) . |
| WO 96/20689 | 7/1996 | (WO) . |
| WO 96/39385 | 12/1996 | (WO) . |
| 98/25883 | * 6/1998 | (WO) . |

OTHER PUBLICATIONS

Amparo, E. C. et al., "Preparation of .alpha.–aminoboronic acid and ester as inhibitors of thrombin", Chemical Abstract, 1996, vol. 125(17), p. 1172, Abstract No. 222432.

Amparo, E.C. et al., "Boronic acid and ester inhibitors of thrombin", Chemical Abstract, 1997, vol. 126(3), p. 594, Abstract No. 31466.

Nagase, H. et al., "Preparation of morphinan derivatives as analgesics and diuretics", Chemical Abstract, 1994, vol. 120(13), p. 1236, Abstract No. 164625.

Tsushima, T. et al., "Preparation of amino acid derivatives as digestive tract hormone antagonists", Chemical Abstract, 1992, vol. 116(25), p. 838, Abstract No. 256040.

Bihovsky et al., "Preparation of benzothiazine– and related heterocyclic group– containing amino as cysteine and serine protease inhibitors", Chemical Abstract, 1998, vol. 129, WO 98/21186, Abstract No. 28214.

Harbeson, S.L. et al., "Stereospecific Synthesis of Peptidyl α–Keto Amides as Inhibitors of Calpain", *J. Med. Chem.*, 1994, 37, 2918–2929.

Lehninger, *Biochemistry*, Secondary Edition, Worth Publishers, Inc., 1975, 73–75.

Meyer, S.L. et al., "Biologically active monomeric and heterodimeric recombinant human calpain produced using the baculovirus expression system", *Biochem. J.*, 1996, 314, 511–519.

Winterbottom et al., "Studies in Chemotherapy. XV. Amides of Pantyoltaurine," *J. Am. Chem. Soc.*, 1947, 69, 1393–1401.

Green, T.W. et al., *Protective Groups in Organic Synthesis*, 2d. Ed., Wiley & Sons, 1991.

*Remington's Pharmaceutical Sciences*, Mark Publishing Company, Easton, PA, 1980.

Bihovsky, R., et al., USpattful, 1999, 110318.

Chatterjee, S., et al. , Caplus 1999, 131:337341.

Chatterjee, S., et al., Caplus, 1999, 131:306757.

Bihovsky, R., et al., Caplus, 1998, 129:28214.

* cited by examiner

*Primary Examiner*—Alan L. Rotman
*Assistant Examiner*—Rita Desai
(74) *Attorney, Agent, or Firm*—Woodcock Washburn Kurtz Mackiewicz & Norris LLP

(57) ABSTRACT

This invention relates to peptide-containing α-ketoamide inhibitors of cysteine and serine proteases, methods for making these compounds, and methods for using the same.

5 Claims, No Drawings

PEPTIDE-CONTAINING α-KETOAMIDE CYSTEINE AND SERINE PROTEASE INHIBITORS

CROSS REFERENCE TO RELATED APPLICATIONS

This application is a divisional of application Ser. No. 09/166,808, filed Oct. 6, 1998, the contents of which are incorporated herein in its entirety which is a claims benefit of U.S. Provisional Application Ser. No. 60/061,309, filed Oct. 7, 1997, the disclosure of which is hereby incorporated herein by reference in its entirety.

FIELD OF THE INVENTION

This invention relates to peptide-containing α-ketoamide inhibitors of cysteine and serine proteases, methods for making these compounds, and methods for using the same.

BACKGROUND OF THE INVENTION

Numerous cysteine and serine proteases have been identified in human tissues. A "protease" is an enzyme which degrades proteins into smaller components (peptides). The terms "cysteine proteaseII and "serine protease" refer to proteases which are distinguished by the presence therein of a cysteine or serine residue which plays a critical role in the catalytic process. Mammalian systems, including humans, normally degrade and process proteins via a variety of enzymes including cysteine and serine proteases. However, when present at elevated levels or when abnormally activated, cysteine and serine proteases may be involved in pathophysiological processes.

For example, calcium-activated neutral proteases ("calpains") comprise a family of intracellular cysteine proteases which are ubiquitously expressed in mammalian tissues. Two major calpains have been identified; calpain I and calpain II. While calpain II is the predominant form in many tissues, calpain I is thought to be the predominant form in pathological conditions of nerve tissues. The calpain family of cysteine proteases has been implicated in many diseases and disorders, including neurodegeneration, stroke, Alzheimer's, amyotrophy, motor neuron damage, acute central nervous system injury, muscular dystrophy, bone resorption, platelet aggregation, cataracts and inflammation. Calpain I has been implicated in excitatory amino-acid induced neurotoxicity disorders including ischemia, hypoglycemia, Huntington's Disease, and epilepsy. The lysosomal cysteine protease cathepsin B has been implicated in the following disorders: arthritis, inflammation, myocardial infarction, tumor metastasis, and muscular dystrophy. Other lysosomal cysteine proteases include cathepsins C, H, L and S. Interleukin-1β converting enzyme ("ICE") is a cysteine protease which catalyzes the formation of interleukin-1β. Interleukin-1β is an immunoregulatory protein implicated in the following disorders: inflammation, diabetes, septic shock, rheumatoid arthritis, and Alzheimer's disease. ICE has also been linked to apoptotic cell death of neurons, which is implicated in a variety of neurodegenerative disorders including Parkinson's disease, ischemia, and amyotrophic lateral sclerosis (ALS).

Cysteine proteases are also produced by various pathogens. The cysteine protease clostripain is produced by *Clostridium histolyticum*. Other proteases are produced by *Trypanosoma cruzi*, malaria parasites *Plasmodium falciparum* and *P. vinckei* and Streptococcus. Hepatitis A viral protease HAV C3 is a cysteine protease essential for processing of picornavirus structural proteins and enzymes.

Exemplary serine proteases implicated in degenerative disorders include thrombin, human leukocyte elastase, pancreatic elastase, chymase and cathepsin G. Specifically, thrombin is produced in the blood coagulation cascade, cleaves fibrinogen to form fibrin and activates Factor VIII; thrombin is implicated in thrombophlebitis, thrombosis and asthma. Human leukocyte elastase is implicated in tissue degenerative disorders such as rheumatoid arthritis, osteoarthritis, atherosclerosis, bronchitis, cystic fibrosis, and emphysema. Pancreatic elastase is implicated in pancreatitis. Chymase, an enzyme important in angiotensin synthesis, is implicated in hypertension, myocardial infarction, and coronary heart disease. Cathepsin G is implicated in abnormal connective tissue degradation, particularly in the lung.

Given the link between cysteine and serine proteases and various debilitating disorders, compounds which inhibit these proteases would be useful and would provide an advance in both research and clinical medicine. The present invention is directed to these, as well as other, important ends.

SUMMARY OF THE INVENTION

The present invention is directed to selected peptide-containing α-ketoamide inhibitors of cysteine and serine proteases represented by the general formula I:

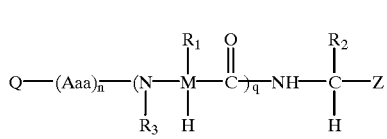

wherein:
Q has the formula G—B—(CHR$^4$), where R$^4$ is independently H or alkyl having from 1 to 4 carbons;
v is 0, 1, or 2;
B is selected from the group consisting of C(=O), OC(=O), S(=O)$_m$, CH$_2$, a bond, NR$^5$C(=O), S(=O)$_m$—A—C(=O), and C(=O)—A—C(=O), where R$^5$ is H or lower alkyl;
m is 0, 1, or 2;
A is lower alkylene or cycloalkylene, optionally substituted with one or more halogen atoms, aryl, or heteroaryl groups;
M is a carbon atom;
G is selected from the group consisting of H, a blocking group, lower alkyl, lower alkenyl, aryl having from about 6 to about 14 carbons, heterocyclyl having from about 5 to about 14 ring atoms, heterocycloalkyl having from about 5 to about 14 ring atoms, arylalkyl having from about 7 to about 15 carbons, heteroarylalkyl, and arylheteroalkyl wherein the aryl portion can be unfused or fused with the heteroalkyl ring, said alkyl, aryl, heterocyclyl, heterocycloalkyl, arylalkyl, heteroarylalkyl, and arylheteroalkyl groups being optionally substituted with one or more J groups;
J is selected from the group consisting of halogen, CN, nitro, lower alkyl, cycloalkyl, heterocycloalkyl, heteroalkyl, halogenated alkyl, aryloxyalkyl, alkylthio, alkylsulfonyl, aryl, heteroaryl, arylalkyl, arylalkyloxy, arylsulfonyl, heteroarylsulfonyl, alkoxycarbonyl, alkoxyalkyl, acyl, alkoxy, hydroxy, carboxy, hydroxyalkyl, amino, alkylamino, and aminoalkyl, said amino group or said amino group of said aminoalkyl or alkylamino group being optionally substituted with an acyl group, an alkoxy group, or with 1 to 3 aryl, lower alkyl, cycloalkyl, or alkoxyalkyl groups; and said aryl, heteroaryl, heterocycloalkyl, and heteroalkyl groups being further optionally substituted by a J group;

each Aaa is independently an amino acid which optionally contains one or more blocking groups;

n is 0, 1, 2, or 3;

$R^1$ and $R^2$ are independently selected from the group consisting of H, alkyl having from one to about 6 carbons, arylalkyl having from about 7 to about 15 carbons, heteroalkyl in which the ring contains from about 5 to about 14 ring atoms, heteroarylalkyl in which the heteroaryl ring contains from about 5 to about 14 ring atoms, alkoxyalkyl, a side chain of a naturally occurring amino acid in the R or S configuration, and $(CH_2)_p$NH-L, said alkyl, arylalkyl, heteroalkyl, heteroarylalkyl, and alkoxyalkyl groups being optionally substituted with one or more J groups;

p is 0, 1, 2, or 3;

L is selected from the group consisting of alkoxycarbonyl having from 2 to about 7 carbons, arylalkoxycarbonyl in which the arylalkoxy group contains about 7 to about 15 carbons, and $S(=O)_2R^6$;

$R^6$ is selected from the group consisting of lower alkyl, and aryl having from about 6 to about 14 carbons;

$R^3$ is selected from the group consisting of H, alkyl having from one to about 6 carbons, arylalkyl having from about 7 to about 15 carbons, heteroalkyl in which the ring contains from about 5 to about 14 ring atoms, heteroarylalkyl in which the heteroaryl ring contains from about 5 to about 14 ring atoms, alkoxyalkyl, a side chain of a naturally occurring amino acid in the R or S configuration, $(CH_2)_p$NH—L, $C(=O)R^7$, $S(=O)_2R^7$, a blocking group, and when combined with the carbon atom to which RI is attached an alkylene group having from 2 to 5 carbons, said alkylene group being optionally substituted with a group selected from the group consisting of aryl, azide, CN, a protected amino group, and $OSO_2$-aryl, said alkyl, arylalkyl, heteroalkyl, heteroarylalkyl, and alkoxyalkyl groups being optionally substituted with one or more J groups;

$R^7$ is selected from the group consisting of aryl having from about 6 to about 14 carbons, heteroaryl having from about 5 to about 14 ring atoms, arylalkyl having from about 7 to about 15 carbons, alkyl having from 1 to about 10 carbons, said aryl, heteroaryl, arylalkyl and alkyl groups being optionally substituted with one or more J groups, heteroalkyl having from 2 to about 7 carbons, alkoxy having from about 1 to about 10 carbons, and amino optionally substituted with 1 or more alkyl groups;

q is 0 or 1;

Z is selected from the group consisting of C(=O)C(=O)NH—X—$A^1$—K and

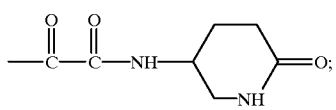

X is a bond or —O—;
$A^1$ is the same as A;

K is selected from the group consisting of $N(R^{10})Y$,

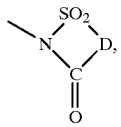

and $SO_2N(R^8)(R^{10})$;

D is a fused aryl or heteroaryl group;

$R^{11}$ is selected from the group consising of alkoxy, aryloxy, and $NHR^{12}$;

$R^{12}$ is selected from the group consisting of H, alkyl, aryl, and heteroaryl, said alkyl, aryl or heteroaryl groups being optionally substituted with one or more J groups;

Y is selected from the group consisting of $SO_2R^8$, $C(=O)NHR^9$, $C(=S)NHR^9$, $C(=NCN)R^{11}$, $C(=NC(=O)NHR^{10})R^{11}$, and $CO_2R^8$;

$R^8$ is selected from the group consisting of alkyl, alkoxy, aryl, and heterocyclyl, said alkyl, alkoxy, aryl, or heterocyclyl groups being optionally substituted with one or more J groups;

$R^9$ is selected from the group consisting of H, alkyl, aryl, and heteroaryl, said alkyl, aryl, or heteroaryl groups being optionally substituted with one or more J groups; or an $R^9$ alkyl group may be combined with an $A^1$ alkylene group to form a N-containing heterocyclic 5- or 6-membered ring;

$R^{10}$ is selected from the group consisting of H and lower alkyl;

or in the moiety $SO_2N(R^8)R^{10}I$, $R^8$ and $R^{10}$ may be combined together with the N atom to which they are attached to form a N-containing heterocyclic 5- or 6-membered ring;

or where $A^1$ is an alkylene group, and K is $N(R^{10})Y$ wherein $R^{10}$ is alkyl, said $R^{10}$ alkyl group may be combined with said $A^1$ alkylene group to form a N-containing heterocyclic 5- or 6-membered ring; or a pharmaceutically acceptable salt thereof.

In some preferred embodiments of the compounds of Formula I, n and v are each 0, q is 1, B is a bond, and G is H. In further preferred embodiments of the compounds of Formula I, $R^1$ is the sidechain of a naturally occurring amino acid. In still further preferred embodiments of the compounds of Formula I, $R^3$ is —S(=C)_2R^8$.

In some preferred embodiments of the compounds of Formula I, $R^2$ is benzyl or alkoxyalkyl. In more preferred embodiments, X is a bond, and Y is $SO_2R^8$. Preferably, $A^1$ is —$CH_2$—$CH_2$—, —$CH_2$—CH($CH_3$)—, or —($CH_3$)CH—$CH_2$—.

In further preferred embodiments of the compounds of Formula I, $R^1$ is a serine sidechain, which is optionally capped with a benzyl group. Preferably, the carbon to which the serine sidechain is attached, designated "M" in Formula I, is a carbon atom in the D configuration.

In preferred embodiments of the compounds of Formula I, $R^2$ is benzyl, $R^7$ is methyl, and $R^8$ is substituted phenyl, unsubstituted phenyl, substituted heteroaryl, or unsubstituted heteroaryl. In particularly preferred embodiments, $R^8$ is aryl, aryl substituted with amino, aryl substituted with heterocyclomethyl, heteroaryl, alkyl substituted with heteroaryl, or heteroaryl substituted with alkylthio, haloalkyl, alkyl, phenylsulfonyl, halogen, aminophenyl, amino, or dialkylaminoalkyl.

In further preferred embodiments of the compounds of Formula I, n, v and q are each 0, B is (C=O), and G is phenyl or lower alkyl, said phenyl or lower alkyl groups being optionally substituted with one or more J groups.

In more preferred embodiments of the invention, n and v are each 0, q is 1, $R^1$ is the side chain of an amino acid in the D- or L-configuration, $R^3$ is $S(=O)_2R^7$, G is H, B is a bond, $R^2$ is benzyl or alkoxyalkyl, X is a bond, and Y is $SO_2R^8$.

In other preferred embodiments, $A^1$ is $CH_2CH_2$, $CH_2CH(CH_3)$, or $(CH_3)CHCH_2$. In more preferred embodiments, $R^1$ is a serine side chain in the D-configuration in which the hydroxyl group is capped with benzyl, $R^2$ is benzyl, $R^7$ is methyl, and $R^8$ is substituted or unsubstituted phenyl or substituted or unsubstituted heteroaryl.

More preferred are the substituents shown for $R_1$–$R_4$, B, G, Aaa, X, $A^1$, Y, n, q and v shown for the compounds in Tables 2, 3, 4 and 5. Especially preferred are the substituents shown for compounds 9, 13, 17, 22, and 29–151.

Some especially preferred embodiments of the compounds of Formula I are shown in Tables 2, 3, 4 and 5, infra, with compounds 9, 13, 17, 22, and 29–151 being particularly preferred.

Because the peptide-containing α-ketoamides of the invention inhibit cysteine proteases and serine proteases, they can be used in both research and therapeutic settings.

In a research environment, preferred compounds having defined attributes can be used to screen for natural and synthetic compounds which evidence similar characteristics in inhibiting protease activity. The compounds can also be used in the refinement of in vitro and in vivo models for determining the effects of inhibition of particular proteases on particular cell types or biological conditions.

In a therapeutic setting, given the connection between cysteine proteases and certain defined disorders, and serine proteases and certain defined disorders, compounds of the invention can be utilized to alleviate, mediate, reduce and/or prevent disorders which are associated with abnormal and/or aberrant activity of cysteine proteases and/or serine proteases.

In preferred embodiments, compositions are provided for inhibiting a serine protease or a cysteine protease comprising a compound of the invention and a pharmaceutically acceptable carrier. In other preferred embodiments, methods are provided for inhibiting serine proteases or cysteine proteases comprising contacting a protease selected from the group consisting of serine proteases and cysteine proteases with an inhibitory amount of a compound of the invention.

Methodologies for making the present peptide-containing α-ketoamide inhibitors are also disclosed. Other useful methodologies will be apparent to those skilled in the art, once armed with the present disclosure. These and other features of the compounds of the subject invention are set forth in more detail below.

DETAILED DESCRIPTION

Disclosed herein are the selected peptide-containing α-ketoamides which are represented by the following formula I:

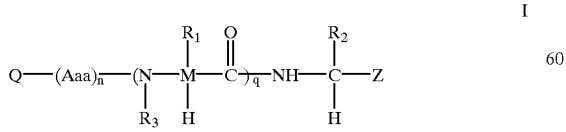

I wherein:

Q has the formula G—B—$(CHR^4)_v$ where $R^4$ is independently H or alkyl having from 1 to 4 carbons;

v is 0, 1, or 2;

B is selected from the group consisting of C(=O), OC(=O), $S(=O)_m$, $CH_2$, a bond, $NR^5C(=O)$, $S(=O)_m$—A—C(=O), and C(=O)—A—C(=O), where $R^5$ is H or lower alkyl;

m is 0, 1, or 2;

A is lower alkylene or cycloalkylene, optionally substituted with one or more halogen atoms, aryl, or heteroaryl groups;

M is a carbon atom;

G is selected from the group consisting of H, a blocking group, lower alkyl, lower alkenyl, aryl having from about 6 to about 14 carbons, heterocyclyl having from about 5 to about 14 ring atoms, heterocycloalkyl having from about 5 to about 14 ring atoms, arylalkyl having from about 7 to about 15 carbons, heteroarylalkyl, and arylheteroalkyl wherein the aryl portion can be unfused or fused with the hetercalkyl ring, said alkyl, aryl, heterocyclyl, heterocycloalkyl, arylalkyl, heteroarylalkyl, and arylheteroalkyl groups being optionally substituted with one or more J groups;

J is selected from the group consisting of halogen, CN, nitro, lower alkyl, cycloalkyl, heterocycloalkyl, heteroalkyl, halogenated alkyl, aryloxyalkyl, alkylthio, alkylsulfonyl, aryl, heteroaryl, arylalkyl, arylalkyloxy, arylsulfonyl, heteroarylsulfonyl, alkoxycarbonyl, alkoxyalkyl, acyl, alkoxy, hydroxy, carboxy, hydroxyalkyl, amino, alkylamino, and aminoalkyl, said amino group or said amino group of said aminoalkyl or alkylamino group being optionally substituted with an acyl group, an alkoxy group, or with 1 to 3 aryl, lower alkyl, cycloalkyl, or alkoxyalkyl groups; and said aryl, heteroaryl, heterocycloalkyl, and heteroalkyl groups being further optionally substituted by a J group;

each Aaa is independently an amino acid which optionally contains one or more blocking groups;

n is 0, 1, 2, or 3;

$R^1$ and $R^2$ are independently selected from the group consisting of H, alkyl having from one to about 6 carbons, arylalkyl having from about 7 to about 15 carbons, heteroalkyl in which the ring contains from about 5 to about 14 ring atoms, heteroarylalkyl in which the heteroaryl ring contains from about 5 to about 14 ring atoms, alkoxyalkyl, a side chain of a naturally occurring amino acid in the R or S configuration, and $(CH_2)_p$NH—L, said alkyl, arylalkyl, heteroalkyl, heteroarylalkyl, and alkoxyalkyl groups being optionally substituted with one or more J groups;

p is 0, 1, 2, or 3;

L is selected from the group consisting of alkoxycarbonyl having from 2 to about 7 carbons, arylalkoxycarbonyl in which the arylalkoxy group contains about 7 to about 15 carbons, and $S(=C)_2R^6$;

$R^6$ is selected from the group consisting of lower alkyl, and aryl having from about 6 to about 14 carbons;

$R^3$ is selected from the group consisting of H, alkyl having from one to about 6 carbons, arylalkyl having from about 7 to about 15 carbons, heteroalkyl in which the ring contains from about 5 to about 14 ring atoms, heteroarylalkyl in which the heteroaryl ring contains from about 5 to about 14 ring atoms, alkoxyalkyl, a side chain of a naturally occurring amino acid in the R or S configuration, $(CH_2)_p$NH—L, $C(=O)R^7$, $S(=)_2R^7$, a blocking group, and when combined with the carbon atom to which $R^1$ is attached an alkylene group having from 2 to 5 carbons, said alkylene group being optionally substituted with a group selected from the group consisting of aryl, azide, CN, a protected amino group, and $OSO_2$-aryl, said alkyl, arylalkyl, heteroalkyl, heteroarylalkyl, and alkoxyalkyl groups being optionally substituted with one or more J groups;

$R^7$ is selected from the group consisting of aryl having from about 6 to about 14 carbons, heteroaryl having from about 5 to about 14 ring atoms, arylalkyl having from about 7 to about 15 carbons, alkyl having from 1 to about 10 carbons, said aryl, heteroaryl, arylalkyl and alkyl groups being optionally substituted with one or more J groups, heteroalkyl having from 2 to about 7 carbons, alkoxy having from about 1 to about 10 carbons, and amino optionally substituted with 1 or more alkyl groups;

q is 0 or 1;

Z is selected from the group consisting of C(=O)C(=O) NH—X—$A^1$—K and

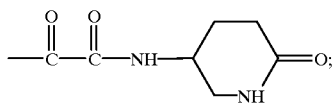

X is a bond or —O—;

$A^1$ is the same as A;

K is selected from the group consisting of $N(R^{10})Y$,

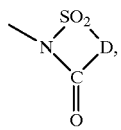

and $SO_2N(R^8)(R^{10})$;

D is a fused aryl or heteroaryl group;

$R^{11}$ is selected from the group consisting of alkoxy, aryloxy, and $NHR^{12}$;

$R^{12}$ is selected from the group consisting of H, alkyl, aryl, and heteroaryl, said alkyl, aryl or heteroaryl groups being optionally substituted with one or more J groups;

Y is selected from the group consisting of $SO_2R^8$, C(=O) $NHR^9$, C(=S) $NHR^9$, C(=NCN) $R^{11}$, C(=NC (=O) $NHR^{10})R^{11}$, and $CO_2R^8$;

$R^8$ is selected from the group consisting of alkyl, alkoxy, aryl, and heterocyclyl, said alkyl, alkoxy, aryl, or heterocyclyl groups being optionally substituted with one or more J groups;

$R^9$ is selected from the group consisting of H, alkyl, aryl, and heteroaryl, said alkyl, aryl, or heteroaryl groups being optionally substituted with one or more J groups;

or an $R^9$ alkyl group may be combined with an $A^1$ alkylene group to form a N-containing heterocyclic 5- or 6-membered ring;

$R^{10}$ is selected from the group consisting of H and lower alkyl;

or in the moiety $SO_2N(R^8)R^{10}$, $R^8$ and $R^{10}$ may be combined together with the N atom to which they are attached to form a N-containing heterocyclic 5- or 6-membered ring;

or where $A^1$ is an alkylene group, and K is $N(R^{10})Y$ wherein $R^{10}$ is alkyl, said $R^{10}$ alkyl group may be combined with said $A^1$ alkylene group to form a N-containing hetrocyclic 5- or 6-membered ring; or a pharmaceutically acceptable salt thereof.

It is recognized that various stereoisomeric forms of the compounds of Formula I may exist. Preferred compounds of the invention have any Aaa groups being a-amino acids in the L-configuration. However, racemates and individual enantiomers and mixtures thereof form part of the present invention.

The carbon atom designated as "M" in the compounds of Formula I can exist in either the D or the L configuration. In some preferred embodiments, M is a carbon atom having the "D" configuration.

As used herein, the term "alkyl" includes straight-chain, and branched hydrocarbon groups such as, for example, methyl, ethyl, propyl, isopropyl, butyl, isobutyl, sec-butyl, tert-butyl, pentyl, 1-ethylpentyl, hexyl, and octyl groups. "Cycloalkyl" groups are cyclic alkyl groups, such as, for example, cyclopropyl, methylcyclopentyl, and cyclohexyl groups. Preferred alkyl groups have 1 to about 10 carbon atoms, most preferably "lower alkyl" of 1 to about 6 carbon atoms. "Alkylene" groups are alkyl groups having two points of attachment; i.e., non-terminal alkyl groups. "Lower alkylene" groups are branched or unbranched alkylene groups of 1 to about 6 carbon atoms such as, for example, ethylene (—$CH_2CH_2$—), propylene, butylene, hexylene, 1-methylethylene, 2-methylethylene, and 2-methylpropylene. "Cycloalkylene" groups are cyclic alkylene groups. "Acyl" groups are alkylcarbonyl groups. "Aryl" groups are aromatic cyclic compounds preferably including but not limited to phenyl, tolyl, naphthyl, anthracyl, phenanthryl, and pyrenyl. Also included within the definition of "aryl" are ring systems having two aromatic rings connected by a bond, such as biphenyl. Preferred aryl groups include phenyl and naphthyl.

The term "carbocyclic", as used herein, refers to cyclic groups in which the ring portion is composed solely of carbon atoms. The term "halogen" refers to F, Cl, Br, and I atoms. The term "arylalkyl" denotes alkyl groups which bear aryl groups, for example, benzyl groups. As used herein, "alkoxy" groups are alkyl groups linked through an oxygen atom. Examples of alkoxy groups include methoxy (—$OCH_3$) and ethoxy (—$OCH_2CH_3$) groups. In general, the term "oxy" when used as a suffix denotes attachment through an oxygen atom. Thus, alkoxycarbonyl groups are carbonyl groups which contain an alkoxy substituent, i.e., groups of general formula —C(=O)—C—R, where R is alkyl. The term "alkoxyalkyl" denotes an alkoxy group attached to an alkyl group. The term "aryloxy" denotes an aryl group linked through an oxygen atom, and the term "arylalkyloxy" denotes an arylalkyl group linked through an oxygen atom.

The terms "heterocycle", "heterocyclyl", and "heterocyclic" refer to cyclic groups in which a ring portion includes at least one heteroatom such as O, N or S. Heterocyclic groups include "heteroaryl" as well as "heteroalkyl" groups. The term "heteroaryl" denotes aryl groups having one or more hetero atoms (e.g., C, N, or S) contained within an aromatic ring. Also included within the definition of "heteroaryl" are ring systems having two aromatic rings connected by a bond, where at least one of the rings contains a hetero atom. Preferred "heteroaryl" groups include pyridyl, pyrimidyl, pyrrolyl, furyl, thienyl, imidazolyl, triazolyl, tetrazolyl, quinolyl, isoquinolyl, benzoimidazolyl, thiazolyl, bipyridyl, pyridylthiophenyl, pyrimidylthiophenyl, benzimidazolyl, isoxazolylthiophenyl, pyrazolylthiophenyl, phthalimido, and benzothiazolyl. The term "heterocycloalkyl" denotes a heterocycle attached through a lower alkyl group. The term "heteroarylalkyl" denotes a heteroaryl group attached through an alkyl group.

As used herein, the term "heteroalkyl" denotes a heterocyclic group which contains at Least one saturated carbon atomn in a heterocyclic ring. Examples of heteroalkyl groups include piperidine, dihydropyridine, and tetrahydroisoquinyl groups. The term "arylheteroalkyl" as used herein denotes a "heteroalkyl" group connected through an aryl group. One preferred example of an arylheteroalkyl group is dibenzo-γ-pyranyl.

As used herein, the term "amino acid" denotes a molecule containing both an amino group and a carboxyl group. As used herein the term "L-amino acid" denotes an α-amino acid having the L-configuration around the α-carbon, that is, a carboxylic acid of general formula CH(COOH)(NH$_2$)—(side chain), having the L-configuration. The term "D-amino acid" similarly denotes a carboxylic acid of general formula CH(COOH)(NH$_2$)—(side chain), having the D-configuration around the α-carbon. Side chains of L-amino acids include naturally occurring and non-naturally occurring moieties. Nonnaturally occurring (i.e., unnatural). amino acid side chains are moieties that are used in place of naturally occurring amino acid sidechains in, for example, amino acid analogs. See, for example, Lehninger, *Biochemistry*, Second Edition, Worth Publishers, Inc, 1975, pages 73–75. One representative amino acid side chain is the lysyl side chain, —(CH$_2$)$_4$—NH$_2$. Other representative a-amino acid side chains are shown below in Table 1.

Functional groups present in the compounds of Formula I may contain blocking groups. Blocking groups are known per se as chemical functional groups that can be selectively appended to functionalities, such as hydroxyl groups, amino groups, thio groups, and carboxyl groups. Protecting groups are blocking groups which can be readily removed from functiorialities. These groups are present in a chemical compound to render such functionality inert to chemical reaction conditions to which the compound is exposed. Any of a variety of protecting groups may be employed with the present invention. Examples of such protecting groups are the benzyloxycarbonyl (Cbz; Z), toluenesulfonyl, t-butoxycarbonyl, methyl ester, and benzyl ether groups. Other preferred protecting groups according to the invention may be found in Greene, T. W. and Wuts, P. G. M., *"Protective Groups in Organic Synthesis"* 2d. Ed., Wiley & Sons, 1991, which is hereby incorporated by reference in its entirety.

Further blocking groups useful in the compounds of the present invention include those that bear acyl, aroyl, alkyl, alkanesulfonyl, arylalkanesulfonyl, or arylsulfonyl substituents on their amino groups. Other useful blocking groups include alkyl ethers, e.g., the methyl ether of serine.

The disclosed compounds of the invention are useful for the inhibition of cysteine proteases and serine proteases. As used herein, the terms "inhibit" and "inhibition" mean having an adverse effect on enzymatic activity. An inhibitory amount is an amount of a compound of the invention effective to inhibit a cysteine and/or serine protease.

TABLE 1

CH$_3$—
HO—CH$_2$—
C$_6$H$_5$—CH$_2$—
HO—C$_6$H$_4$—CH$_2$—

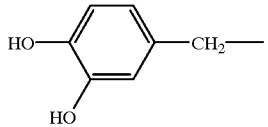

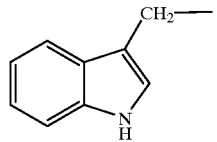

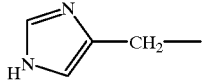

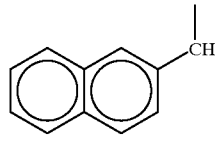

HS—CH$_2$—
HO$_2$C—CH(NH$_2$)—CH$_2$S—S—CH$_2$—
CH$_3$—CH$_2$—
CH$_3$S—CH$_2$—CH$_2$—

CH$_3$—CH$_2$—S—CH$_2$—CH$_2$—
HO—CH$_2$—CH$_2$—
CH$_3$—CH(OH)—

HO$_2$C—CH$_2$—NHC(=O)—CH$_2$—

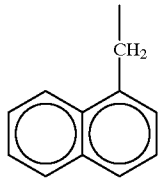

HO$_2$C—CH$_2$—CH$_2$—
NH$_2$C(=O)—CH$_2$—CH$_2$—

(CH$_3$)$_2$—CH—
(CH$_3$)$_2$—CH—CH$_2$—
CH$_3$—CH$_2$—CH$_2$—
H$_2$N—CH$_2$—CH$_2$—CH$_2$—

H$_2$N—C(=NH)—NH—CH$_2$—CH$_2$—CH$_2$—
H$_2$N—C(=O)—NH—CH$_2$—CH$_2$—CH$_2$—
CH$_3$—CH$_2$—CH(CH$_3$)—
CH$_3$—CH$_2$—CH$_2$—CH$_2$—
H$_2$N—CH$_2$—CH$_2$—CH$_2$—CH$_2$—

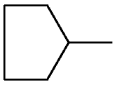

Pharmaceutically acceptable salts of the cysteine and serine protease inhibitors also fall within the scope of the compounds as disclosed herein. The term "pharmaceutically acceptable salts" as used herein means an inorganic acid addition salt such as hydrochloride, sulfate, and phosphate, or an organic acid addition salt such as acetate, maleate, fumarate, tartrate, and citrate. Examples of pharmaceutically acceptable metal salts are alkali metal salts such as sodium salt and potassium salt, alkaline earth metal salts such as magnesium salt and calcium salt, aluminum salt, and zinc salt. Examples of pharmaceutically acceptable organic amine addition salts are salts with morpholine and piperidine. Examples of pharmaceutically acceptable amino acid addition salts are salts with lysine, glycine, and phenylalanine.

Compounds provided herein can be formulated into pharmaceutical compositions by admixture with pharmaceutically acceptable nontoxic excipients and carriers. As noted above, such compositions may be prepared for use in parenteral administration, particularly in the form of liquid solutions or suspensions; or oral administration, particularly in the form of tablets or capsules; or intranasally, particularly in the form of powders, nasal drops, or aerosols; or dermally, via, for example, transdermal patches; or prepared in other suitable fashions for these and other forms of administration as will be apparent to those skilled in the art.

The composition may conveniently be administered in unit dosage form and may be prepared by any of the methods well known in the pharmaceutical art, for example, as described in Remington's Pharmaceutical Sciences (Mack Pub. Co., Easton, Pa., 1980). Formulations for parenteral administration may contain as common excipients sterile water or saline, polyalkylene glycols such as polyethylene glycol, oils and vegetable origin, hydrogenated naphthalenes and the like. In particular, biocompatible, biodegradable lactide polymer, lactide/glycolide copolymer, or polyoxyethylene-polyoxypropylene copolymers may be useful excipients to control the release of the active compounds. Other potentially useful parenteral delivery systems for these active compounds include ethylene-vinyl acetate copolymer particles, osmotic pumps, implantable infusion systems, cyclodextrins and liposomes. Formulations for inhalation administration contain as excipients, for example, lactose, or may be aqueous solutions containing, for example, polyoxyethylene-9-lauryl ether, glycocholate and deoxycholate, or oily solutions for administration in the form of nasal drops, or as a gel to be applied intranasally. Formulations for parenteral administration may also include glycocholate for buccal administration, a salicylate for rectal administration, or citric acid for vaginal administration. Formulations for transdermal patches are preferably lipophilic emulsions.

The materials for this invention can be employed as the sole active agent in a pharmaceutical or can be used in combination with other active ingredients which could facilitate inhibition of cysteine and serine proteases in diseases or disorders.

The concentrations of the compounds described herein in a therapeutic composition will vary depending upon a number of factors, including the dosage of the drug to be administered, the chemical characteristics (e.g., hydrophobicity) of the compounds employed, and the route of administration. In general terms, the compounds of this invention may be provided in effective inhibitory amounts in an aqueous physiological buffer solution containing about 0.1 to 10% w/v compound for parenteral administration. Typical dose ranges are from about 1ug/kg to about 1 g/kg of body weight per day; a preferred dose range is from about 0.01 mg/kg to 100 mg/kg of body weight per day. Such formulations typically provide inhibitory amounts of the compound of the invention. The preferred dosage of drug to be administered is likely, however, to depend on such variables as the type or extent of progression of the disease or disorder, the overall health status of the particular patient, the relative biological efficacy of the compound selected, and formulation of the compound excipient, and its route of administration.

As used herein, the term "contacting" means directly or indirectly causing at least two moieties to come into physical association with each other. Contacting thus includes physical acts such as placing the moieties together in a container, or administering moieties to a patient. Thus, for example administering a compound of the invention to a human patient evidencing a disease or disorder associated with abnormal and/or aberrant activity of such proteases falls within the scope of the definition of the term "contacting".

The invention is further illustrated by way of the following examples which are intended to elucidate the invention. These examples are not intended, nor are they to be construed, as limiting the scope of the disclosure.

EXAMPLES

General Methods.

Thin layer chromatography was performed on silica gel plates (MK6F 60A, size 1×3 in, layer thickness 250 $\mu$m, Whatman Inc.). Preparative thin layer chromatography was performed on silica gel plates (size 20×20 in, layer thickness 1000 micron, Analtech). Preparative column chromatography was carried out using Merck silica gel, 40–63 $\mu$m, 230–400 mesh. $^1$H NMR spectra were recorded on a GE QE Plus instrument (300 MHZ) using tetramethylsilane as internal standard. Electrospray mass spectra were recorded on a VG platform II instrument (Fisons Instruments).

Compounds of the invention were prepared following one of the General Methods A, B, C or D.

Example 1
Preparation of Compound 9 by General Method A

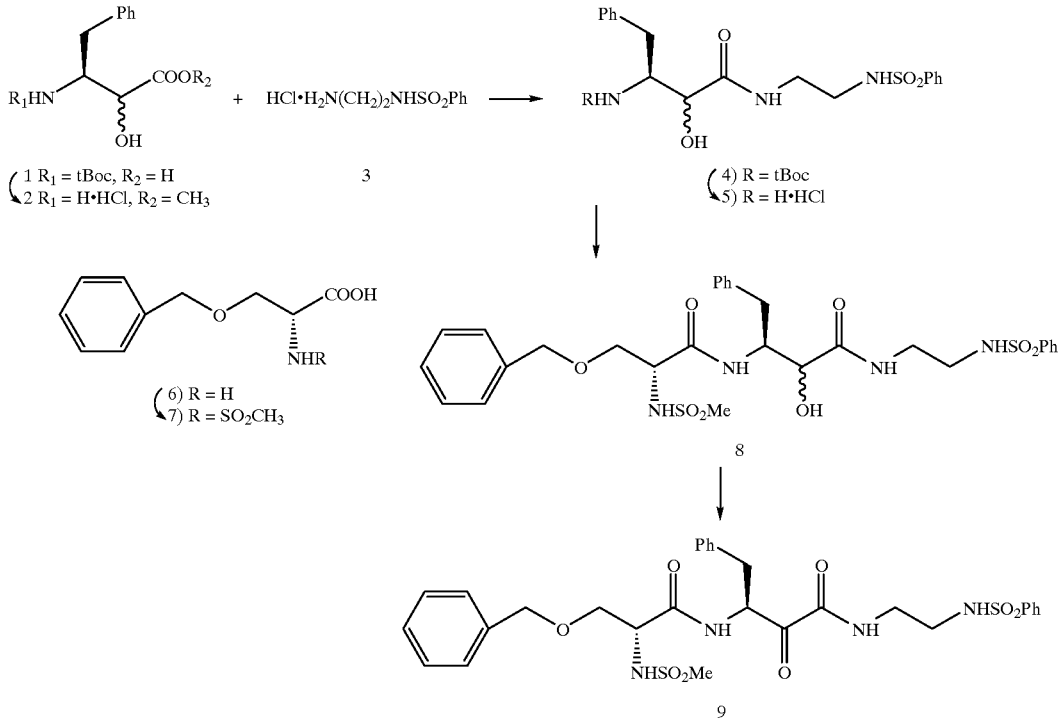

General Method A

Preparation of Compound 1

This compound and related hydroxy acids used in this study were synthesized following a general procedure of Harbeson et al, *J. Med. Chem.* 1994, 37, 2918–2929, which is incorporated herein by reference in its entirety.

Preparation of Compound 2

To a cooled (−10° C.) solution of compound 1 (4.30 g, 0.015 mol) in anhydrous methanol (50 mL) was added slowly thionyl chloride (3.20 mL). After 0.5 hour, the cooling bath was removed, the mixture was stirred for an additional 16 hours and concentrated to give a residue which on trituration with ethyl acetate (30 mL) gave a white solid. The solid was separated by filtration and dried to give 3.50 g of compound 2 which was used directly in the next step; MS m/e 210(M+H).

Preparation of Compound 3

The preparation of this compound is shown in General Method E.

Preparation of Compound 4

To a cooled (0° C.) solution of compound 1 (1.00 g, 0.0034 mol) in anhydrous DMF (20 mL) was added NMM (1.40 g, 0.014 mmol) followed by 1-HOBt (0.54 g, 0.0040 mmol) and BOP (1.80 g, 0.0040 mmol). The mixture was stirred for 15 minutes and to it was added compound 3 (0.75g, 0.0032 mmol). The cooling bath was removed and the mixture was stirred for 4 hours, poured into ice-water (200 mL), and extracted into ethyl acetate (3×100 mL). The organic layer was washed with 2% citric acid solution (2×50 mL), 2% sodium bicarbonate solution (2×50 mL), brine (1×50 mL), and it was dried over anhydrous sodium sulfate. Solvent evaporation under reduced pressure gave a crude solid which was washed several times with n-pentane to produce 1.30 g of compound 4.

Compound 4: white solid (diastereomeric mixture); $^1$H-NMR (DMSO-$d_6$) δ 7.90 and 7.65 (2 sets of t, 1H), 7.75 (d, 2H), 7.55 (q, 2H), 7.15 (m, 6H), 6.55 and 5.80 (2 sets of d, 1H), 3.90 (m, 2H), 3.30 (d, 1H), 3.10 (m, 2H), 2.75 (m, 2H), 2.50 (m, 3H), 1.20 (s, 9H). MS m/e 478(M+H), 500(M+Na).

Preparation of Compound 5

To a solution of compound 4 (0.40 g, 0.84 mmol) in 1,4-dioxane (15 mL) was added 4 N HCl in dioxane (15 mL). The reaction mixture was stirred at room temperature for 2 hours, then concentrated at reduced pressure to give a residue which was washed several times with ethyl acetate and dried under vacuum to give 0.30 g of compound 5; $^1$H-NMR (DMSO-$d_6$) showed complete absence of tBoc peak at δ 1.20 ppm; MS m/e 378 (M+H). This material was used directly in the next step.

Preparation of Compound 7

To a mixture of D-Ser(Bn) (compound 6, 1.00g, 5 mmol) and 1 N NaOH (10 mL, 10 mmol) at 0° C. was slowly added methanesulfonyl chloride (0.80 g, 7.69 mmol). After 0.5 hour, the cooling bath was removed, the mixture was stirred overnight and acidified (pH~2–3) with 2 N HCl. The aqueous layer was extracted into ethyl acetate (3×50 mL). The combined organic layer was washed with water (1×20 mL) and brine (1×20 mL), and dried over $MgSO_4$. Solvent evaporation gave a residue which was redissolved in methylene chloride (10 mL); addition of hexanes produced a white solid which was filtered and dried to give 1.02 g of compound 7.

Preparation of Compound 8

This compound was prepared by coupling compound 7 and compound 5, using NMM/HOBt/BOP as coupling agents, following the procedure described above for the preparation of compound 4. In some of the related examples, EDCI/HOBt were used as coupling agents.
Preparation of Compound 9

To a cooled (0° C.) solution of compound 8 (0.31 g, 0.49 mmol) in anhydrous methylene chloride (10 mL) was added Dess-Martin periodinane reagent (0.425 g, 1.00 mmol). The cooling bath was removed and the mixture was stirred for an additional 1 hour. The solution was then diluted with methylene chloride (10 mL), and washed with 10% sodium thiosulfate solution (5×5 ml), saturated sodium bicarbonate solution (2×5 mL), and brine (1×5 mL), and dried over anhydrous sodium sulfate. Solvent removal under reduced pressure gave a residue which was washed with n-pentane (10 mL) and dried under vacuum to produce 0.178 g of compound 9; $^{1}$H-NMR spectrum revealed a minor amount of epimerization had taken place.

Compound 9: white solid; $^{1}$H-NMR (DMSO-$d_6$) δ 8.75 (t, 1H), 8.60 and 8.50 (2 doublets, 1H), 7.75 (d, 2H), 7.65–7.00 (a series of m, 15H), 5.25 (broad m, 1H), 4.45 and 4.235 (2 singlets, 2H), 4.15 (m, 1H), 3.35–2.60 (a series of m, 8H), 3.35 and 3.25 (2 singlets, 3H) MS m/e 631(M+H), 653(M+Na).

Example 2
Preparation of Compound 13 by General Method B

General Method B

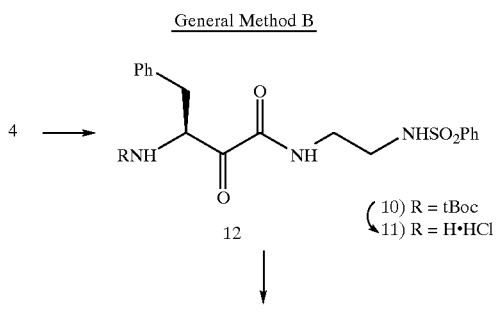

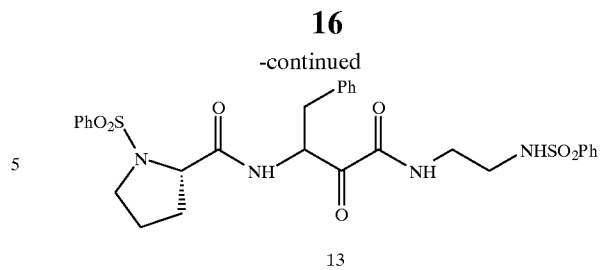

In General Method B, compound 4, prepared as described above, was oxidized by Dess-Martin periodinane reagent to generate compound 10 which on tBoc-deprotection (2 N HCl in dioxane) produced the amine-salt, compound 11. Coupling (NMM/HOBt/BOP) of compound 11 with N-phenylsulfonyl-(L)-Pro (compound 12) yielded compound 13. Purification was achieved by passing a solution of the crude material in methylene chloride through Sep-Pak® Vac 6 cc (1 g) silica cartidge (Waters Corporation, Milford, Mass.), eluting with methylene chloride, followed by various combinations of methylene chloride and ethyl acetate. Harbeson et al. (*J. Med. Chem.* 1994, 37, 2918–2929) reported that silica gel chromatography of a ketoamide epimerizes the chiral center at $P_1$.

Compound 13: white solid; $^{1}$H-NMR (CDCl$_3$) δ 7.90–7.00 (a series of m, 18H), 5.40 and 5.30 (2 multiplets, 1H), 4.10 (m, 1H), 3.50–3.00 (m, 8H), 1.90–1.40 (m, 4H). MS m/e 613 (M+H), 635 (M+Na)

Example 3
Preparation of Compound 17 by General Method C

In General Method C, compound 2 was coupled (NMM/HOBt/BOP) with L-Cbz-Leu to give compound 14 which was hydrolyzed (aq. NaOH) to compound 15. Coupling (NMM/HOBt/BOP) of compound 15 with compound 3 gave compound 16 which underwent Dess-Martin oxidation to generate compound 17.

General Method C

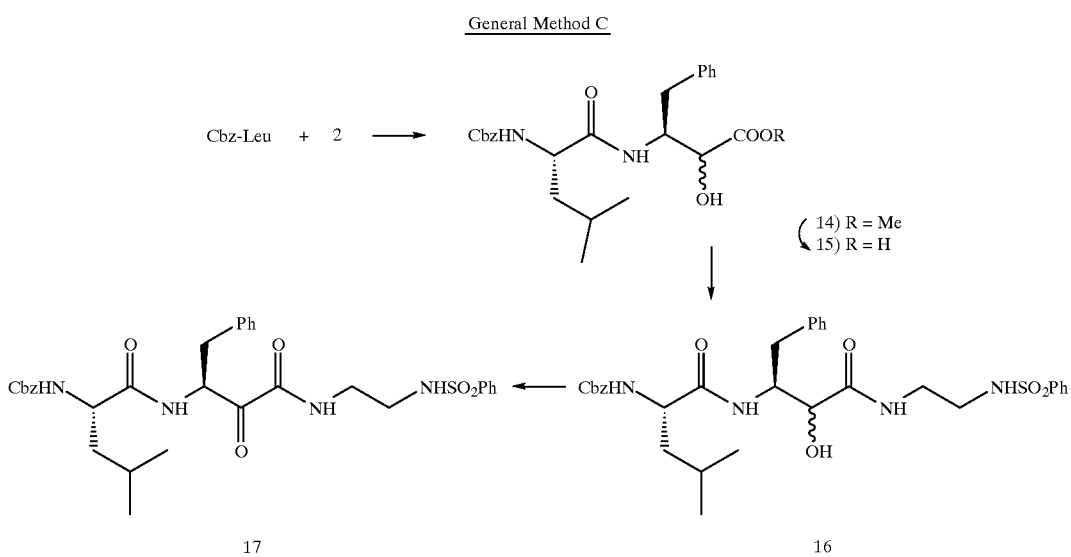

Compound 17: white solid; $^{1}$H-NMR (CDCl$_3$) δ 7.85 (d, 2H), 7.60–7.00 (a series of m, 15H), 6.60 (d, 1H), 5.40 (m, 1H), 5.20 (q, 1H), 5.10 (s, 2H), 4.10 (broad, 1H), 3.50–3.00 (a series of m, 6H), 1.65–1.30 (m, 3H), 0.90 (d, 6H). MS m/e 623 (M+H), 645 (M+Na).

Example 4
Preparation of Compound 22 by General Method D

In General Method D, compound 7 was coupled (NMM/HOBt/BOP) with compound 2 to generate compound 18 which underwent Dess-Martin oxidation to generate compound 19. Hydrolysis (LiOH, MeOH—H$_2$O) of compound 19 gave compound 20 which was coupled (NMM/HOBt/BOP) with compound 21 to give compound 22. Compound 22 was purified by silica gel chromatography.

Compound 22: white solid; MS m/e 646(M+H), 668(M+Na).

Preparation of Compound 24

To a solution of 1,2-ethylenediamine (compound 23, 10.80 g, 12.00 mL, 0.18 mol) in THF (30 mL) was added slowly BOC-ON (22.10 g, 0.09 mol) in THF (70 mL) over a period of 4 hours. The reaction mixture was stirred overnight, concentrated on a rotavapor, and taken up into water (150 mL). The aqueous layer was acidified (pH~5–6) with solid citric acid monohydrate, washed with ether (3×50 mL) and then treated (at 0° C.) with 6 N NaOH solution to make it basic (pH~12–13). The basic solution was extracted into ethyl acetate (3×100 mL), and the combined ethyl acetate layer was dried (MgSO$_4$) and concentrated to gen-

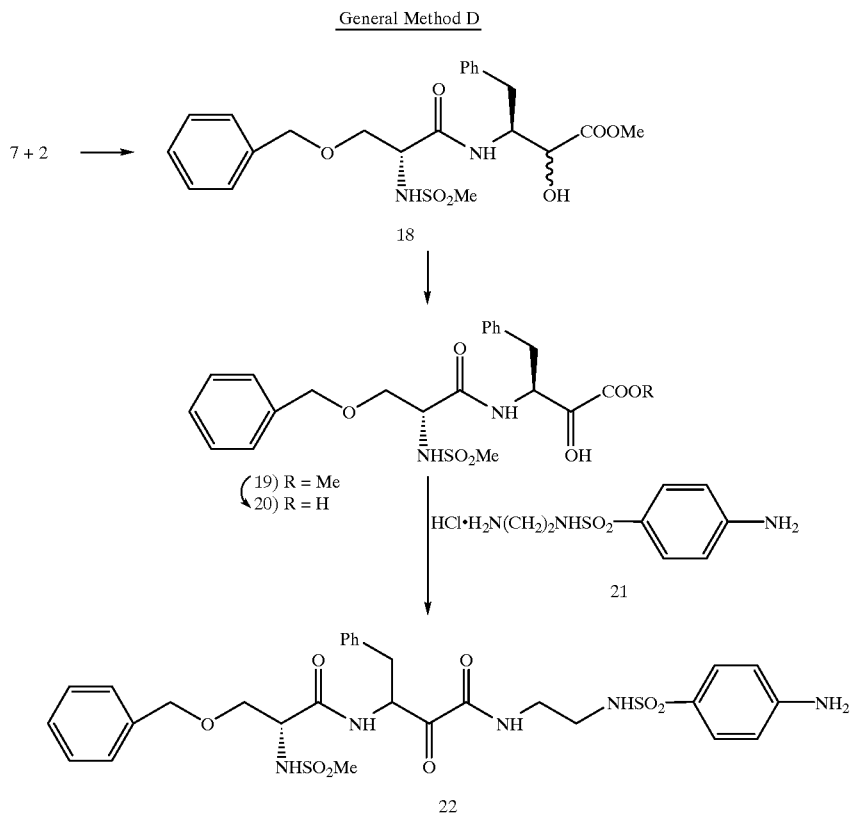

Preparation of Intermediates

Example 5

The preparation of a representative example of an amine (compound 3), containing a terminal sulfonamide moiety, is shown in General Method E.

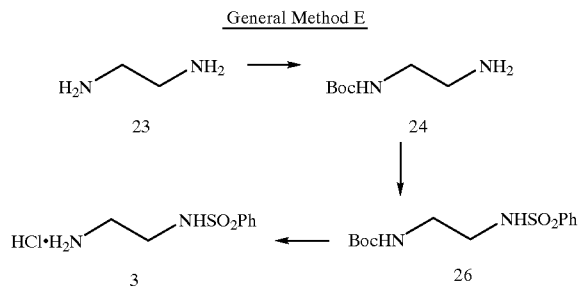

erate 7.23 g of monoprotected diamine, compound 24. Compound 24: viscous liquid; $^1$H-NMR (CDCl$_3$) δ 5.00 (broad, 1H), 3.20 (broad q, 2H), 2.80 (t, 2H), 1.45 (s, 9H), 1.25 (broad, 2H).

Preparation of Compound 25

A cooled (0–5° C.) solution of compound 24 (0.321 g, 0.002 mol) in methylene chloride (5 mL) was treated sequentially with triethylamine (0.243 g, 0.33 mL, 0.0024 mol) and benzenesulfonyl chloride (0.423 g, 0.30 mL, 0.0024 mol). The ice-bath was removed and the mixture was stirred for an additional 0.5 hour, washed successively with water (2×5 mL), cold (0–5° C.) 0.5 N HCl (1×5 mL), 2% NaHCO$_3$ solution (1×5 mL), and brine (1×5 mL). The solution was dried (MgSO$_4$) and the solvent was evaporated to give a residue which was washed several times with n-pentane. A total of 0.60 g of the sulfonamide derivative, compound 25, was obtained.

Compound 25: white solid, mp 92–95° C.; Rf (TLC, 5% methanol in methylene chloride) 0.55; $^1$H-NMR (CDCl$_3$) δ 7.85 (d, 2H), 7.55 (m, 3H), 5.30 (broad d, 1H), 4.85 (broad, 1H), 3.25 (broad q, 2H), 3.10 (broad q, 2H), 1.40 (s, 9H).

Preparation of Compound 3

A solution of compound 25 (0.560 g, 0.0019 mol) in 1,4-dioxane (4 mL) was treated with 4 N HCl in dioxane (4 mL). The mixture was stirred at room temperature for 1 hour and concentrated at the rotavapor. The residue was washed several times with ethyl acetate and dried under vacuum to give 0.40 g of compound 3.

Compound 3: white solid, mp 178–180° C.; $^1$H-NMR (DMSO-d$_6$) δ 8.20–8.00 (broad t, 4H), 7.80 (d, 2H), 7.60 (m, 3H), 2.95 (broad q, 2H), 2.80 (broad, 2H).

Example 6

Preparation of Compound 28

The preparation of a representative example of an intermediate amine (compound 28) containing a terminal biaryl sulfonamide moiety is shown in General Method F.

General Method F

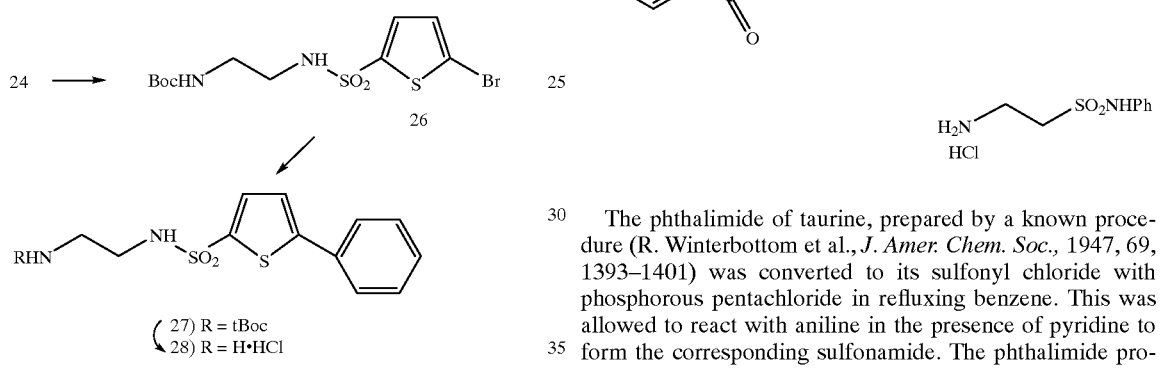

(27) R = tBoc
(28) R = H·HCl

A mixture of compound 26 (prepared from compound 24 and 5-bromothiophene-2-sulfonyl chloride, following the same general procedure as described above for the preparation of compound 25, 0.50 g, 1 eqv), dimethoxyethane (10 mL), 2 M Na$_2$CO$_3$ (5 eqv), phenylboronic acid (1.40 eqv) and Pd(PPh$_3$)$_4$ (0.04 eqv) was heated at 135 IC for 2.5 hours. The reaction mixture was concentrated at the rotavapor, and the residue was taken up into water (20 mL). The aqueous layer was acidified with citric acid and extracted into methylene chloride (3×20 mL). The combined organic layer was washed with water (1×10 mL) and brine (1×10 mL). It was dried (MgSO$_4$) and concentrated to a small volume. Trituration of the residue with hexanes gave a solid which was separated by filtration and dried under vacuum to produce 0.37 g of compound 27; $^1$H-NMR (CDCl$_3$) δ 7.60–7.20 (a series of m, 7H), 5.35 (broad, 1H), 4.85 (broad, 1H), 3.30 (m, 2H), 3.20 (m, 2H), 1.40 (s, 9H). For a general description of this reaction procedure, see Miyaura et al., *Chem. Rev.* 1995, 95, 2457–2483.

Compound 27 was converted to compound 28 following the procedure described for the preparation of compound 3.

Example 7

Preparation of Taurine Sulfonamide Intermediate

The preparation of a representative taurine sulfonamide intermediate is shown in General Method G.

General Method G

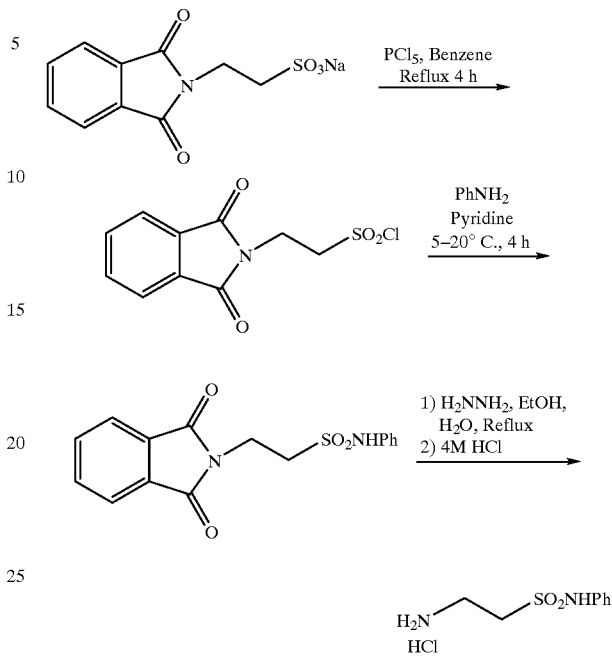

The phthalimide of taurine, prepared by a known procedure (R. Winterbottom et al., *J. Amer. Chem. Soc.*, 1947, 69, 1393–1401) was converted to its sulfonyl chloride with phosphorous pentachloride in refluxing benzene. This was allowed to react with aniline in the presence of pyridine to form the corresponding sulfonamide. The phthalimide protecting group was then removed by refluxing with hydrazine and the resulting taurine sulfonamide was isolated as its hydrochloride.

Example 8

Syntheses of compounds 29 through 50 in Tables 2 and 3 were carried out using the designated general methods, as described, and the appropriate starting materials.

Example 9

Inhibition of Cysteine Protease Activity

To evaluate inhibitory activity, stock solutions (40 times concentrated) of each compound to be tested were prepared in 100% anhydrous DMSO and 5 μl of each inhibitor preparation were aliquoted into each of three wells of a 96-well plate. Recombinant human calpain I, prepared by the method of Meyer et al. (*Biochem. J.* 1996, 314: 511–519; incorporated herein by reference in its entirety), was diluted into assay buffer (i.e., 50mM Tris, 50mM NaCl, 1mM EDTA, 1 mM EGTA, and 5mM 8-mercaptoethanol, pH 7.5, including 0.2 mM Succ-Leu-Tyr-MNA), and 175 μl was aliquoted into the same wells containing the independent inhibitor stocks as well as to positive control wells containing 5 μl DMSO, but no compound. To start the reaction, 20 μl of 50 mM CaCl$_2$ in assay buffer was added to all wells of the plate, excepting three, which were used as background signal baseline controls. Substrate hydrolysis was monitored every 5 minutes for a total of 30 minutes. Substrate hydrolysis in the absence of inhibitor was linear for up to 15 minutes.

Inhibition of calpain I activity was calculated as the percent decrease in the rate of substrate hydrolysis in the presence of inhibitor relative to the rate in its absence. Comparison between the inhibited and control rates was made within the linear range for substrate hydrolysis. The $IC_{50}$s of inhibitors (concentration yielding 50% inhibition) were determined from the percent decrease in rates of substrate hydrolysis in the presence of five to seven different concentrations of the test compound. The results were plotted as percent inhibition versus log inhibitor concentration, and the $IC_{50}$ was calculated by fitting the data to the four-parameter logistic equation shown below using the program GraphPad Prism (GraphPad Software, Inc., San Diego, Calif.).

$$y=d+[(a-d)/(1+(x/c)^b)]$$

The parameters a, b, c, and d are defined as follows: a is % inhibition in the absence of inhibitor, b is the slope, c is the $IC_{50}$, and d is the E inhibition at an infinite concentration of inhibitor.

Results are presented in Tables 2, 3, 4 and 5 below.

TABLE 2

Inhibitory Activity of Linear α-Ketoamides

| Cmp. No. | W | $R_2$ | R | Calpain $IC_{50}$ nM | Prep. Method | MS (M + 1)+ |
|---|---|---|---|---|---|---|
| 9 | Ms-D-Ser(Bn) | Bn | Ph | 16 | A | 631 |
| 13 | PhSO$_2$-L-Pro | Bn | Ph | (78%)** | B | 613 |
| 17 | Cbz-L-Leu | Bn | Ph | 11 | C | 623 |
| 22 | Ms-D-Ser(Bn) | Bn | 4-aminophenyl | 42 | D | 646 |
| 29 | Ms-D-Ser(Bn) | Bn | thienyl-pyridyl | 14 | A | 714 |
| 30 | PhSO$_2$-L-Phe | Bn | Ph | (97%)** | B | 663 |
| 31 | Ms-D-Ser(Bn) | Bn | 3-pyridyl | 29 | A | 632 |
| 32 | Ms-D-Ser(Bn) | Bn | thienyl-isoxazolyl | 10 | A | 704 |
| 33 | Ms-D-Ser(Bn) | Bn | thienyl-pyrimidinyl-SCH$_3$ | 17 | A | 761 |

TABLE 2-continued
Inhibitory Activity of Linear α-Ketoamides
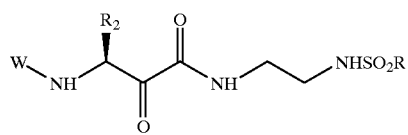
| Cmp. No. | W | $R_2$ | R | Calpain $IC_{50}$ nM | Prep. Method | MS $(M + 1)+$ |
|---|---|---|---|---|---|---|
| 34 | Ms-D-Ser(Bn) | Bn | 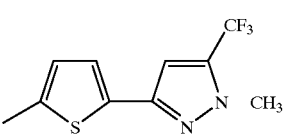 | 25 | A | 786 $(M + 2)^+$ |
| 35 | Ms-D-Ser(Bn) | Bn | $CH_3$ | 91 | A | 569 |
| 36* | Ms-D-Ser(Bn) | $CH_2OMe$ | 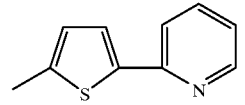 | 14 | A | 668 |
| 37 | Ms-D-Ser(Bn) | Bn | 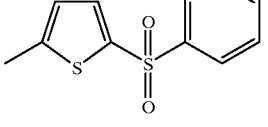 | 18 | C | 777 |
| 38* | Ms-D-Ser(Bn) | $CH_2OMe$ | Ph | (100%)* | A | 585 |
| 39 | Ms-D-Ser(Bn) | Bn | 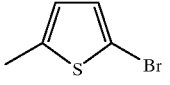 | 22 | C | 715, 717 $^{79}Br$, $^{81}Br$ |
| 40 | Ms-D-Ser(Bn) | Bn | 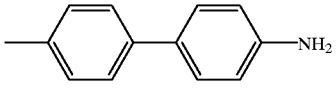 | 63 | D | 722 |
| 41 | Ms-D-Ser(Bn) | Bn | 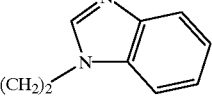 | (88%)** | D | 699 |
| 42 | Ms-D-Ser(Bn) | Bn | 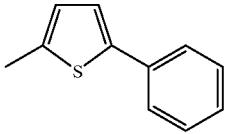 | 14 | C | 712(M)+ |
| 43 | Ms-D-Ser(Bn) | Bn | 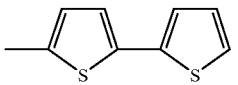 | 11 | C | 718(M)+ |

TABLE 2-continued

Inhibitory Activity of Linear α-Ketoamides

W-NH-CH(R₂)-C(=O)-C(=O)-NH-CH₂CH₂-NHSO₂R

| Cmp. No. | W | R₂ | R | Calpain IC₅₀ nM | Prep. Method | MS (M + 1)+ |
|---|---|---|---|---|---|---|
| 44 | Ms-D-Ser(Bn) | Bn | 5-methylthiophen-2-yl-(3-aminophenyl) | 31 | D | 729 (M + 2)⁺ |
| 45 | Ms-D-Ser(Bn) | Bn | 4-(CH₂NMe₂)-phenyl-methyl | 64 | D | 688 |
| 46 | Ms-D-Ser(Bn) | Bn | —(CH₂)₂—(4-pyridyl)·HCl | 144 | D | 660 |

*2:1 ratio of diastereomers.
**Percent inhibition @ 10 μM

TABLE 3

Inhibitory Activity of Branched-Chain α-Ketoamides

| Ex. No. | D | Calpain IC₅₀ nM | Prep. Method | MS (M + 1) |
|---|---|---|---|---|
| 47 | CH(CH₃)(CH₂CH₃)-NHSO₂Ph (L) | 26 | A | 645 |
| 48 | CH(CH₃)(CH₂CH₃)-NHSO₂Ph (D) | 43 | A | 645 |
| 49 | CH(CH₃)(CH₂-NHSO₂Ph) (L) | 32 | A | 646 (M + 2) |
| 50 | CH₂CH₂N(CH₃)SO₂Ph | (100%)** | C | 645 |

Compounds listed in Table 4 were prepared by the general methods A–G described above.

TABLE 4

Inhibitory Activity of α-Ketoamides

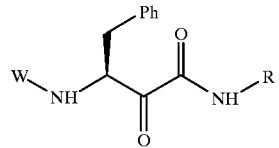

| Ex. No. | W | R | Calpain IC$_{50}$ nM | MS (M + 1) |
|---|---|---|---|---|
| 51 | Ms-D-Ser (Bn) | CH$_2$CH$_2$NHSO$_2$-(3-(2-NH$_2$-thiazol-4-yl)Ph) | 29 | 729 |
| 52 | Ms-D-Ser (Bn) | CH$_2$CH$_2$NHSO$_2$-(5-(3-formylphenyl)thiophene-2-yl) | 5 | 741 |
| 53 | Ms-D-Ser (Bn) | CH$_2$CH$_2$NHC(=N—CN)OPh | 15 | 635 |
| 54 | Ms-D-Ser (Bn) | CH$_2$CH$_2$NHSO$_2$(5-(3-(Me$_2$NCH$_2$)phenyl)thiophene-2-yl) | 12 | 770 |
| 55 | Ms-D-Ser (Bn) | 3-Boc-NH-cyclohexane | 42 | 645 |
| 56 | Ms-D-Ser (Bn) | CH$_2$CH$_2$NHSO$_2$(5-(3-(morpholinoCH$_2$)phenyl)thiophene-2-yl) | 18 | 812 |
| 57 | Ms-D-Ser (Bn) | CH$_2$CH$_2$NHSO$_2$(4-(MorpholinoCH$_2$)Ph) | 18 | 730 |
| 58 | Ms-D-Ser (Bn) | CH$_2$CH$_2$NHSO$_2$(5-(3-(N-Me-piperazinyl-CH$_2$)phenyl)thiophene-2-yl) | 21 | 825 |
| 59 | Ms-D-Ser (Bn) | CH$_2$CH$_2$NHSO$_2$(5-(3-(HOCH$_2$)phenyl)thiophene-2-yl)(2 diast) | 35 | 765 (M + Na) |
| 60 | Ms-D-Ser (Bn) | CH$_2$CH$_2$SO$_2$NHPh | 47 | 631 |
| 61 | Ms-D-Ser (Bn) | CH$_2$CH$_2$SO$_2$NH(4-CF$_3$Ph) | 32 | 699 |
| 62 | Ms-D-Ser (Bn) | (CH$_2$)$_3$SO$_2$NHPh | 18 | 645 |
| 63 | Ms-D-Ser (Bn) | (CH$_2$)$_3$SO$_2$NH(4-CF$_3$Ph) | 23 | 713 |
| 64 | Ms-D-Ser (Bn) | 6-ketopiperidin-3-yl | (33)* | 545 |
| 65 | Ms-D-Ser (Bn) | CH$_2$CH$_2$N(Me)SO$_2$-(5-(3-formylphenyl)thiophene-2-yl) | 19 | 755 |
| 66 | Ms-D-Thr (Bn) | CH$_2$CH$_2$NHSO$_2$(5-pyrid-2-ylthiophene-2-yl) | 12 | 728 |
| 67 | Ms-D-Ser (Bn) | —N(Me)SO$_2$-(5-isoxazol-3-yl-thiophene-2-yl) | 21 | 718 |
| 68 | Ms-(D,L)-Phenylgly | CH$_2$CH$_2$NHSO$_2$(5-pyrid-2-ylthiophene-2-yl) | 21 | 670 |
| 69 | Ms-(D,L)-Phenylgly | CH$_2$CH$_2$NHSO$_2$Ph | 80 | 587 |
| 70 | Ms-D-Thr (Bn) | CH$_2$CH$_2$NHSO$_2$(5-(3-(morpholinoCH$_2$)phenyl)thiophene-2-yl) (Mixture of diastereomers) | 23 | 826 |
| 71 | Ms-D-Phe | CH$_2$CH$_2$NHSO$_2$(5-pyrid-2-ylthiophene-2-yl) | 18 | 684 |
| 72 | Ms-D-Ser (Bn) | CH$_2$CH$_2$NHSO$_2$(5-(3-Fluorophenyl)thiophene-2-yl) (Mixture of diastereomers) | 18 | 731 |
| 73 | Ms-D-Ser (Bn) | (CH$_2$)$_3$SO$_2$NHOCH$_3$ | 87 | 597 (M − 1) |
| 74 | Ms-D-Ser (Bn) | CH$_2$CH$_2$NHSO$_2$-(5-(3-Nitrophenyl)thiophene-2-yl) (Mixture of diastereomers) | 15 | 758 |
| 75 | Ms-D-Ser (Bn) | CH$_2$CH$_2$NHSO$_2$-(5-(3-Methylphenyl)thiophene-2-yl) (Mixture of diastereomers) | 36 | 727 |
| 76 | Ms-D-Ser (Bn) | CH$_2$CH$_2$NHSO$_2$(5-(3-(AcNH)phenyl)thiophene-2-yl) (Mixture of diastereomers) | 11 | 792 (M + Na) |
| 77 | Ms-D-Ser (Bn) | CH$_2$CH$_2$NHSO$_2$(5-(3-(CH$_3$CO)phenyl)thiophene-2-yl) (Mixture of diastereomers) | 10 | 777 (M + Na) |
| 78 | Ms-D-Ser (Bn) | 1-(4-(Morpholinomethyl)benzenesulfonyl)piperidin-4-yl) (Mixture of diastereomers) | 48 | 770 |
| 79 | Ms-D-Ser | CH$_2$CH$_2$NHSO$_2$((4- | 11 | 847 |

TABLE 4-continued

Inhibitory Activity of α-Ketoamides

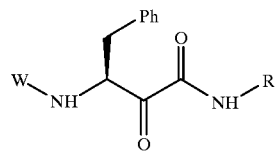

| Ex. No. | W | R | Calpain IC$_{50}$ nM | MS (M + 1) |
|---|---|---|---|---|
|  | (Bn) | (CH$_3$COPh)piperazin-1-yl)CH$_2$Ph) (Mixture of diastereomers) |  |  |
| 80 | Ms-D-Ser (Bn) | (CH$_2$)$_3$SO$_2$NH-morpholin-4-yl | 169 | 652 (M − 1) |
| 81 | Ms-D-Ser (Bn) | (CH$_2$)$_3$SO$_2$-morpholin-4-yl | 124 | 639 |
| 82 | Ms-D-Ser (Bn) | CH$_2$CH$_2$NHSO$_2$-(5-(4-Methoxyphenyl)thiophene-2-yl) (Mixture of diastereomers) | 13 | 765 (M + Na) |
| 83 | Ms-D-Ser (Bn) | CH$_2$CH$_2$CH$_2$-Saccharin | 48 | 657 |
| 84 | Ms-D-Ser (Bn) | CH$_2$CH$_2$NHSO$_2$((4-(PhCH$_2$)piperazin-1-yl)CH$_2$Ph) | 23 | 819 |
| 85 | Ms-D-Ser (Bn) | CH$_2$CH$_2$NHSO$_2$((4-(CH$_3$CO)piperazin-1-yl)CH$_2$Ph) | 14 | 771 |
| 86 | Ms-D-Ser (Bn) | CH$_2$CH$_2$NHSO$_2$-(5-Me$_2$N-naphth-1-yl) | 49 | 724 |
| 87 | Ms-D-Ser (Bn) | CH$_2$CH$_2$NHSO$_2$-benzothiophene-2-yl | 23 | 687 |
| 88 | Cbz-Leu-Leu | CH$_2$CH$_2$NHSO$_2$(5-pyrid-2-ylthiophene-2-yl) | 33 | 819 |
| 89 | Ms-D-Ser (Bn) | CH$_2$CH$_2$NHSO$_2$((4-Pyrid-2-yl)piperazin-1-yl)CH$_2$Ph) (Mixture of diastereomers) | 21 | 806 |
| 90 | Ms-D-Ser (Bn) | CH$_2$CH$_2$NHSO$_2$-(5-(4-formylphenyl)thiophene-2-yl) | 17 | 741 |
| 91 | Ms-D-Ser (Bn) | CH$_2$CH$_2$NHSO$_2$(4-(2-(MeOCH$_2$)PyrrolidinylCH$_2$)Ph) | 19 | 758 |
| 92 | Ms-D-Ser (Bn) | (CH$_2$)$_5$NHSO$_2$(5-pyrid-2-ylthiophene-2-yl) (Mixture of diastereomers) | 12 | 756 |
| 93 | Ms-D-Ser (Bn) | CH$_2$CH$_2$NHSO$_2$(5-(2-(morpholinoCH$_2$)phenyl)thiophene-2-yl) | 40 | 812 |
| 94 | Ms-D-Ser (Bn) | CH$_2$CH$_2$NHSO$_2$(5-(4-(morpholinoCH$_2$)phenyl)thiophene-2-yl) | 22 | 812 |
| 95 | Ms-D-Ser (Bn) | CH$_2$CH$_2$NHSO$_2$(5-(3-(piperidinylCH$_2$)phenyl)thiophene-2-yl) | 30 | 810 |
| 96 | Ms-D-Ser (Bn) | CH$_2$CH$_2$NHSO$_2$(2-acetamido-4-methylthiazol-5-yl) | 23 | 709 |
| 97 | Ms-D-Ser (Bn) | CH$_2$CH$_2$NHSO$_2$(1-phenylsulfonylpiperidin-4-yl) | 32 | 671 |
| 98 | Ms-D-Ser (Bn) | CH$_2$CH$_2$NHSO$_2$-(5-(2-formylphenyl)thiophene-2-yl) | 24 | 741 |
| 99 | Ms-D-Ser (Bn) | CH$_2$CH$_2$NHSO$_2$((CH$_3$O)CH$_3$NCH$_2$Ph) (Mixture of diastereomers) | 21 | 704 |
| 100 | Ms-D-Ser (Bn) | CH$_2$CH$_2$NHSO$_2$(4-ethylpiperazin-1-yl)CH$_2$Ph) (Mixture of diastereomers) | 21 | 756 |
| 101 | Ms-D-Ser (Bn) | CH$_2$CH$_2$NHSO$_2$(5-(3-(Et$_2$NCH$_2$)phenyl)thiophene-2-yl) | 22 | 798 |
| 102 | Ms-D-Ser (Bn) | CH$_2$CH$_2$NHSO$_2$(5-(3-(Cyclohexyl(Me)NCH$_2$)phenyl)thiophene-2-yl) | 36 | 838 |
| 103 | Ms-D-Ser (Bn) | CH$_2$CH$_2$NHSO$_2$(5-(3-(pyrrolidinylCH$_2$)phenyl)thiophene-2-yl) | 24 | 796 |
| 104 | Ms-D-Ser (Bn) | CH$_2$CH$_2$NHSO$_2$(5-(3-cyanophenyl)thiophene-2-yl) | 10 | 738 |
| 105 | Ms-D-Ser (Bn) | CH$_2$CH$_2$NHSO$_2$(4-(4-acetamidophenoxy)CH$_2$Ph) | 14 | 816 (M + Na) |
| 106 | Ms-D-Ser (Bn) | CH$_2$CH$_2$NHSO$_2$(5-(3-(azetidinylCH$_2$)phenyl)thiophene-2-yl) | 44 | 782 |
| 107 | Ms-D-Ser (Bn) | 1-(5-pyridin-2-ylthiophene-2-yl-SO$_2$)Piperidin-4-yl) (Mixture of diastereomers) | 23 | 754 |

TABLE 4-continued

Inhibitory Activity of α-Ketoamides

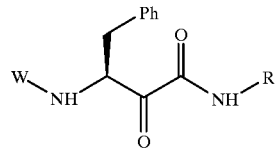

| Ex. No. | W | R | Calpain IC$_{50}$ nM | MS (M + 1) |
|---|---|---|---|---|
| 108 | Ms-D-Ser (Bn) | CONHCH$_2$CH$_2$NHSO$_2$(5-(3-(N-ethyl-N-methylaminomethyl)phenyl)thiophene-2-yl) | 10 | 784 |
| 109 | Ms-D-Ser (Bn) | CH$_2$CH$_2$NHSO$_2$(5-(3-(bis(2-methoxyethyl)aminomethyl)phenyl)thiophene-2-yl) | 22 | 858 |
| 110 | Ms-D-Ser (Bn) | CH$_2$CH$_2$NHSO$_2$(5-(3-cyanophenyl)thiophene-2-yl) (Mixture of diastereomers) | 11 | 738 |
| 111 | Ms-D-Ser (Bn) | CH$_2$CH$_2$NHSO$_2$(4-(3-pyrrolin-1-yl)CH$_2$Ph) (Mixture of diastereomers) | 73 | 712 |
| 112 | Ms-D-Ser (Bn) | CH$_2$CH$_2$NHSO$_2$((4-(CH$_3$SO$_2$)piperazin-1-yl)CH$_2$Ph) | 37 | 807 |
| 113 | Ms-D-Ser (Bn) | CH$_2$CH$_2$NHSO$_2$((4-pyrimid-2-yl)piperazin-1-yl)CH$_2$Ph | 24 | 807 |
| 114 | Ms-D-Ser (Bn) | CH$_2$CH$_2$NHSO$_2$(5-(3-(thiomorpholinoCH$_2$)phenyl)thiophene-2-yl) | 33 | 828 |
| 115 | Ms-D-Ser (Bn) | CH$_2$CH$_2$NHSO$_2$(5-(3-(4-ketopiperidinylCH$_2$)phenyl)thiophene-2-yl) | 16 | 824 |
| 116 | Ms-L-Ser (Bn) | CH$_2$CH$_2$NHSO$_2$Ph | 100 | 631 |

*Percent inhibition @ 0.1 μM
Ms = methylsulfonyl

TABLE 5

Inhibitory Activity of Achiral P$_2$ Mimetic α-Ketoamides

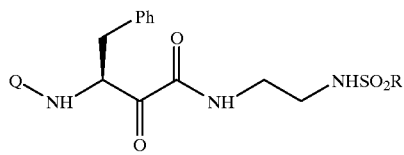

| Ex. No. | Q | R | Calpain IC$_{50}$ nM | Synthesis Method | MS (M + 1)$^+$ |
|---|---|---|---|---|---|
| 117 | Benzoyl | 5-methyl-thiophene-2-pyridine | 800 | A | 563 |
| 118 | 2,6-Dichlorobenzoyl | 5-methyl-thiophene-2-pyridine | 36 | A | 631, 633 |

TABLE 5-continued

Inhibitory Activity of Achiral P$_2$ Mimetic α-Ketoamides

| Ex. No. | Q | R | Calpain IC$_{50}$ nM | Synthesis Method | MS (M + 1)$^+$ |
|---|---|---|---|---|---|
| 119 | 2,6-Dichloro-3-methylbenzoyl | 5-methylthiophene-2-pyridyl | 61 | A | 645 |
| 120 | 2,6-Difluorobenzoyl | 5-methylthiophene-2-pyridyl | 20 | A | 599 |
| 121 | 2,4,6-Trifluorobenzoyl | 5-methylthiophene-2-pyridyl | 85 | A | 618 |
| 122 | 2,3,4,5,6-Pentafluoro-benzoyl | 5-methylthiophene-2-pyridyl | 28 | A | 653 |
| 123 | 3,4-Methylenedioxy-benzoyl | 5-methylthiophene-2-pyridyl | >1000 | A | 607 |
| 124 | 2,5-Dichlorobenzoyl | 5-methylthiophene-2-pyridyl | 68 | A | 631, 633 |
| 125 | 2-Chloro-5-methoxybenzoyl | 5-methylthiophene-2-pyridyl | 65 | A | 627 |
| 126 | 3,5-bis(trifluoromethyl)benzoyl | 5-methylthiophene-2-pyridyl | 600 | A | 699 |

TABLE 5-continued

Inhibitory Activity of Achiral P₂ Mimetic α-Ketoamides

| Ex. No. | Q | R | Calpain IC$_{50}$ nM | Synthesis Method | MS (M + 1)⁺ |
|---|---|---|---|---|---|
| 127 | 2,6-Dimethylbenzoyl | 5-methylthien-2-yl-pyridine | 178 | A | 591 |
| 128 | 2,6-Dichloronicotinoyl | 5-methylthien-2-yl-pyridine | 80 | A | 634, 636 |
| 129 | 2,6-Dichlorobenzoyl | 5-methylthien-2-yl-benzaldehyde | 21 | A | 658, 660 |
| 130 | 2,6-Dichlorobenzoyl | 5-methylthien-2-yl-benzyl-NHAc | 20 | A | 687, 689 |
| 131 | 2,6-Dichlorobenzoyl | 5-methylthien-2-yl-benzyl-morpholine | 29 | A | 729, 731 |
| 132 | 2,6-Dichlorobenzoyl | 4-methylbenzyl-piperazine-2-pyridyl | 83 | A | 723, 725 |
| 133 | 2,6-Dichlorobenzoyl | 5-methylthien-2-yl-benzonitrile | 11 | A | 655, 657 |
| 134 | 2,6-Dichlorobenzoyl | 4-methylbenzyl-piperazine-Ac | 100 | A | 688, 690 |

TABLE 5-continued
Inhibitory Activity of Achiral P$_2$ Mimetic α-Ketoamides
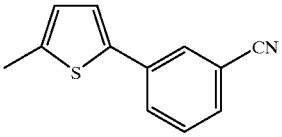
| Ex. No. | Q | R | Calpain IC$_{50}$ nM | Synthesis Method | MS (M + 1)$^+$ |
|---|---|---|---|---|---|
| 135 | 2,6-Difluorobenzoyl | 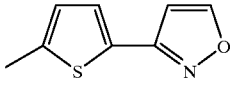 | 22 | A | 645 (M + Na) |
| 136 | 2,6-Difluorobenzoyl | 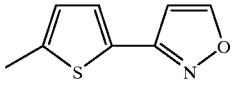 | 62 | A | 611 (M + Na) |
| 137 | 2,6-Diethylbenzoyl | 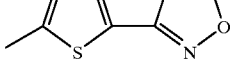 | 145 | A | 631 (M + Na) |
| 138 | 2,6-Dimethoxybenzoyl | 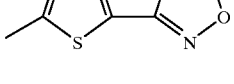 | 4000 | A | 613 |
| 139 | 2-Isopropylbenzoyl | 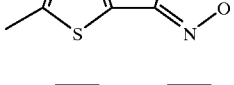 | 168 | A | 595 |
| 140 | 2-Chloro-6-fluorobenzoyl | 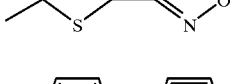 | 58 | A | 605 |
| 141 | 2-Fluoro-6-trifluoro-methylbenzoyl | 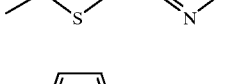 | 58 | A | 639 |
| 142 | 2,3,4,5,6-Pentafluoro-benzoyl | 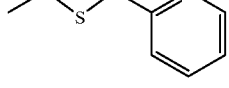 | 32 | A | 643 |
| 143 | 2-Methylpropanoyl | 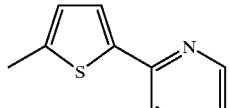 | 1500 | A | 529 |
| 144 | 3-Methylbutanoyl |  | 590 | A | 543 |

TABLE 5-continued

Inhibitory Activity of Achiral P₂ Mimetic α-Ketoamides

| Ex. No. | Q | R | Calpain IC$_{50}$ nM | Synthesis Method | MS (M + 1)⁺ |
|---|---|---|---|---|---|
| 145 | 4-Methylpentanoyl | 5-methylthiophene-2-yl-pyridine | 29 | A | 557 |
| 146 | 3-Cyclopentylpropanoyl | 5-methylthiophene-2-yl-pyridine | 1000 | A | 583 |
| 147 | E-3-Hexenoyl | 5-methylthiophene-2-yl-pyridine | 1000 | A | 555 |
| 148 | 4-Phenylpentanoyl | 5-methylthiophene-2-yl-pyridine | 87 | A | 641 (M + Na) |
| 149 | 4-Phenylbutanoyl | 5-methylthiophene-2-yl-pyridine | 1500 | A | 627 (M + Na) |
| 150 | 4-Methylpentanoyl | 5-methylthiophene-2-yl-(3-cyanophenyl) | 15 | A | 603 (M + Na) |
| 151 | 3-Cyclopentylpropanoyl | 5-methylthiophene-2-yl-(3-cyanophenyl) | 420 | A | 607 |

As those skilled in the art will appreciate, numerous changes and modifications may be made to the preferred embodiments of the invention without departing from the spirit of the invention. It is intended that all such variations fall within the scope of the invention.

It is intended that each of the patents, applications, and printed publications mentioned in this specification be hereby incorporated by reference in their entirety.

What is claimed is:

1. A compound having the Formula:

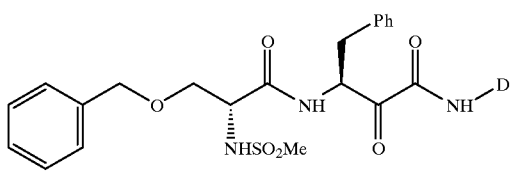

wherein D is CH$_2$CH$_2$N(CH$_3$)SO$_2$Ph or has one of the formulas:

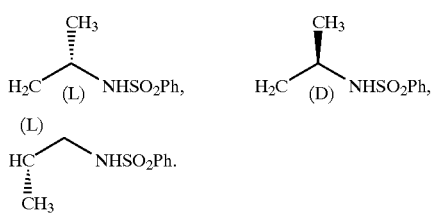

2. A compound having the Formula:

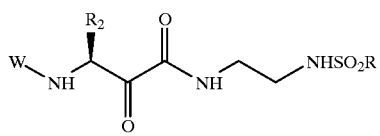

wherein:

R$_2$ is independently selected from the group consisting of Bn and CH$_2$OMe; and W and R are independently selected from the group consisting of Ms-D-Ser(Bn), Ph, PhSO$_2$-L-Pro, Cbz-L-Leu,

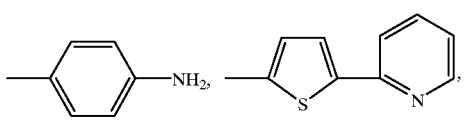

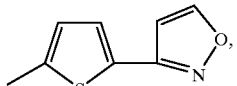

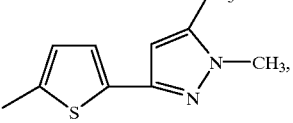

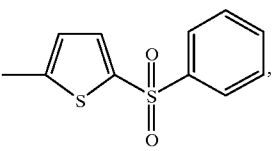

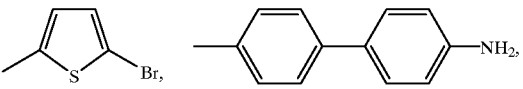

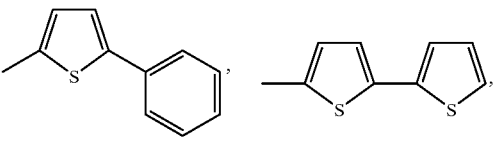

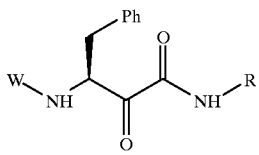

3. A compound having the formula:

wherein W and R are independently selected from the group consisting of Ms-D-Ser (Bn), CH$_2$CH$_2$NHSO$_2$—(3-(2-NH$_2$-thiazol-4-yl)Ph), CH$_2$CH$_2$NHSO$_2$-(5-(3-formylphenyl)thiophene-2-yl), CH$_2$CH$_2$NHSO$_2$(5-(3-(Me$_2$NCH$_2$)phenyl)thiophene-2-yl), CH$_2$CH$_2$NHSO$_2$ (5-(3-(morpholinoCH$_2$)phenyl)thiophene-2-yl), CH$_2$CH$_2$NHSO$_2$(4-(MorpholinoCH$_2$)Ph), CH$_2$CH$_2$NHSO$_2$ (5-(3-(N-Me-piperazinyl-CH$_2$) phenyl)thiophene-2-yl), CH$_2$CH$_2$NHSO$_2$(5-(3-(HOCH$_2$)phenyl)thiophene-2-yl), CH$_2$CH$_2$SO$_2$NHPh, CH$_2$CH$_2$SO$_2$NH(4-CF$_3$Ph), (CH$_2$)$_3$SO$_2$NHPh, (CH$_2$)$_3$SO$_2$NH(4—CF$_3$Ph), CH$_2$CH$_2$N(Me)SO$_2$-(5-(3-formylphenyl)thiophene-2-yl), Ms-D-Thr (Bn), CH$_2$CH$_2$NHS0$_2$(5-pyrid-2-ylthiophene-2-yl), —N(Me)SO$_2$-(5-isoxazol-3-yl-thiophene-2-yl), Ms-(D,L)-Phenylgly, CH$_2$CH$_2$NHSO$_2$(5-pyrid-2-ylthiophene-2-yl), CH$_2$CH$_2$NHSO$_2$Ph, Ms-D-Thr (Bn), CH$_2$CH$_2$NHSO$_2$(5-(3-(morpholinoCH$_2$)phenyl) thiophene-2-yl), Ms-D-Phe, CH$_2$CH$_2$NHSO$_2$(5-pyrid-2-ylthiophene-2-yl), CH$_2$CH$_2$NHSO$_2$(5-(3-Fluorophenyl)thiophene-2-yl), CH$_2$CH$_2$NHSO$_2$-(5-(3-Nitrophenyl)thiophene-2-yl), CH$_2$CH$_2$NHSO$_2$-(5-(3-Methylphenyl)thiophene-2-yl), CH$_2$CH$_2$NHSO$_2$ (5-(3-(AcNH)phenyl)thiophene-2-yl), CH$_2$CH$_2$NHSO$_2$(5-(3-

(CH₃CO)phenyl)thiophene-2-yl), CH₂CH₂NHSO₂-(5-(4-Methoxyphenyl)thiophene-2-yl), Cbz-Leu-Leu, CH₂CH₂NHSO₂ (5-pyrid-2-ylthiophene-2-yl), CH₂CH₂NHSO₂-(5-(4-formylphenyl)thiophene-2-yl), (CH₂)₅NHSO₂(5-pyrid-2-ylthiophene-2-yl), CH₂CH₂NHSO₂(5-(2-(morpholinoCH₂)phenyl)thiophene-2-yl), CH₂CH₂NHSO₂(5-(4-(morpholinoCH₂)phenyl)thiophene-2-yl), CH₂CH₂NHSO₂(5-(3-(piperidinylCH₂)phenyl)thiophene-2-yl), CH₂CH₂NHSO₂-(5-(2-formylphenyl)thiophene-2-yl), CH₂CH₂NHSO₂ (5-(3-(Et₂NCH₂)phenyl) thiophene-2-yl, CH₂CH₂NHSO₂ (5-(3-(Cyclohexyl (Me)NCH₂)phenyl)thiophene-2-yl), CH₂CH₂NHSO₂ (5-(3-(pyrrolidinylCH₂)phenyl)thiophene-2-yl), CH₂CH₂NHSO₂(5-(3-cyanophenyl)thiophene-2-yl), CH₂CH₂NHSO₂(5-(3-(azetidinylCH₂)phenyl)thiophene-2-yl), CONHCH₂CH₂NHSO₂(5-(3-(N-ethyl-N-methylaminomethyl)phenyl)thiophene-2-yl), CH₂CH₂NHSO₂(5-(3-(bis(2-methoxyethyl)aminomethyl)phenyl)thiophene-2-yl), CH₂CH₂NHSO₂ (5-(3-cyanophenyl)thiophene-2-yl), CH₂CH₂NHSO₂ (5-(3-(thiomorpholinoCH₂)phenyl)thiophene-2-yl), CH₂CH₂NHSO₂(5-(3-(4-ketopiperidinylCH₂)phenyl)thiophene-2-yl), Ms-L-Ser (Bn), and CH₂CH₂NHSO₂Ph.

4. The compound of claim 2 wherein W, R₂ and R are selected in accordance with the following table:

| | W | R₂ | R |
|---|---|---|---|
| 1 | Ms-D-Ser(Bn) | Bn | Ph |
| 2 | PhSO₂-L-Pro | Bn | Ph |
| 3 | Cbz-L-Leu | Bn | Ph |
| 4 | Ms-D-Ser(Bn) | Bn | 4-aminotolyl |
| 5 | Ms-D-Ser(Bn) | Bn | 5-methyl-2-(pyrid-2-yl)thiophene |
| 6 | PhSO₂-L-Phe | Bn | Ph |
| 7 | Ms-D-Ser(Bn) | Bn | 5-methyl-2-(isoxazol-3-yl)thiophene |
| 8 | Ms-D-Ser(Bn) | Bn | 5-methyl-2-(2-SCH₃-pyrimidin-4-yl)thiophene |
| 9 | Ms-D-Ser(Bn) | Bn | 5-methyl-2-(5-CF₃-1-CH₃-pyrazol-3-yl)thiophene |
| 10 | Ms-D-Ser(Bn) | CH₂OMe | 5-methyl-2-(pyrid-2-yl)thiophene |
| 11 | Ms-D-Ser(Bn) | Bn | 5-methyl-2-(phenylsulfonyl)thiophene |
| 12 | Ms-D-Ser(Bn) | CH₂OMe | Ph |
| 13 | Ms-D-Ser(Bn) | Bn | 2-bromo-5-methylthiophene |
| 14 | Ms-D-Ser(Bn) | Bn | 4'-amino-4-methylbiphenyl |
| 15 | Ms-D-Ser(Bn) | Bn | 5-methyl-2-phenylthiophene |
| 16 | Ms-D-Ser(Bn) | Bn | 5-methyl-2,2'-bithiophene |
| 17 | Ms-D-Ser(Bn) | Bn | 5-methyl-2-(3-aminophenyl)thiophene |
| 18 | Ms-D-Ser(Bn) | Bn | 4-(CH₂NMe₂)-methylphenyl |

5. The compound of claim 3 wherein W and R are selected in accordance with the following table:

| | W | R |
|---|---|---|
| 1 | Ms-D-Ser(Bn) | CH₂CH₂NHSO₂-(3-(2-NH₂-thiazol-4-yl)Ph) |
| 2 | Ms-D-Ser(Bn) | CH₂CH₂NHSO₂-(5-(3-formylphenyl)thiophene-2-yl) |
| 3 | Ms-D-Ser(Bn) | CH₂CH₂NHSO₂(5-(3-(Me₂NCH₂)phenyl)thiophene-2-yl) |
| 4 | Ms-D-Ser(Bn) | CH₂CH₂NHSO₂(5-(3-(morpholinoCH₂)phenyl)thiophene-2-yl) |

| | W | R |
|---|---|---|
| 5 | Ms-D-Ser(Bn) | $CH_2CH_2NHSO_2$(4-(MorpholinoCH$_2$)Ph) |
| 6 | Ms-D-Ser(Bn) | $CH_2CH_2NHSO_2$(5-(3-(N-Me-piperazinyl-CH$_2$)phenyl)thiophene-2-yl) |
| 7 | Ms-D-Ser(Bn) | $CH_2CH_2NHSO_2$(5-(3-(HOCH$_2$)phenyl)thiophene-2-yl) |
| 8 | Ms-D-Ser(Bn) | $CH_2CH_2SO_2NHPh$ |
| 9 | Ms-D-Ser(Bn) | $CH_2CH_2SO_2NH$(4-CF$_3$Ph) |
| 10 | Ms-D-Ser(Bn) | $CH_2CH_2N(Me)SO_2$-(5-(3-formylphenyl)thiophene-2-yl) |
| 11 | Ms-D-Thr(Bn) | $CH_2CH_2NHSO_2$(5-pyrid-2-ylthiophene-2-yl) |
| 12 | Ms-(D, L)-Phenylgly | $CH_2CH_2NHSO_2$(5-pyrid-2-ylthiophene-2-yl) |
| 13 | Ms-(D, L)-Phenylgly | $CH_2CH_2NHSO_2Ph$ |
| 14 | Ms-D-Thr(Bn) | $CH_2CH_2NHSO_2$(5-(3-(morpholinoCH$_2$)phenyl)thiophene-2-yl) |
| 15 | Ms-D-Phe | $CH_2CH_2NHSO_2$(5-pyrid-2-ylthiophene-2-yl) |
| 16 | Ms-D-Ser(Bn) | $CH_2CH_2NHSO_2$(5-(3-Fluorophenyl)thiophene-2-yl) |
| 17 | Ms-D-Ser(Bn) | $CH_2CH_2NHSO_2$-(5-(3-Nitrophenyl)thiophene-2-yl) |
| 18 | Ms-D-Ser(Bn) | $CH_2CH_2NHSO_2$(5-(3-Methylphenyl)thiophene-2-yl) |
| 19 | Ms-D-Ser(Bn) | $CH_2CH_2NHSO_2$(5-(3-(AcNH)phenyl)thiophene-2-yl) |
| 20 | Ms-D-Ser(Bn) | $CH_2CH_2NHSO_2$(5-(3-(CH$_3$CO)phenyl)thiophene-2-yl) |
| 21 | Ms-D-Ser(Bn) | $CH_2CH_2NHSO_2$-(5-(4-Methoxyphenyl)thiophene-2-yl) |
| 22 | Cbz-Leu-Leu | $CH_2CH_2NHSO_2$(5-pyrid-2-ylthiophene-2-yl) |
| 23 | Ms-D-Ser(Bn) | $CH_2CH_2NHSO_2$-(5-(4-formylphenyl)thiophene-2-yl) |
| 24 | Ms-D-Ser(Bn) | $CH_2CH_2NHSO_2$(4-(2-(MeOCH$_2$)PyrrolidinylCH$_2$)Ph) |
| 25 | Ms-D-Ser(Bn) | $CH_2CH_2NHSO_2$(5-(2-(morpholinoCH$_2$)phenyl)thiophene-2-yl) |
| 26 | Ms-D-Ser(Bn) | $CH_2CH_2NHSO_2$(5-(4-(morpholinoCH$_2$)phenyl)thiophene-2-yl) |
| 27 | Ms-D-Ser(Bn) | $CH_2CH_2NHSO_2$(5-(3-(piperidinylCH$_2$)phenyl)thiophene-2-yl) |
| 28 | Ms-D-Ser(Bn) | $CH_2CH_2NHSO_2$-(5-(2-formylphenyl)thiophene-2-yl) |
| 29 | Ms-D-Ser(Bn) | $CH_2CH_2NHSO_2$(5-(3-(Et$_2$NCH$_2$)phenyl)thiophene-2-yl) |
| 30 | Ms-D-Ser(Bn) | $CH_2CH_2NHSO_2$(5-(3-(Cyclohexyl(Me)NCH$_2$)phenyl)thiophene-2-yl) |
| 31 | Ms-D-Ser(Bn) | $CH_2CH_2NHSO_2$(5-(3-(pyrrolidinylCH$_2$)phenyl)thiophene-2-yl) |
| 32 | Ms-D-Ser(Bn) | $CH_2CH_2NHSO_2$(5-(3-cyanophenyl)thiophene-2-yl) |
| 33 | Ms-D-Ser(Bn) | $CH_2CH_2NHSO_2$(5-(3-(azetidinylCH$_2$)phenyl)thiophene-2-yl) |
| 34 | Ms-D-Ser(Bn) | $CONHCH_2CH_2NHSO_2$(5-(3-(N-ethyl-N-methylaminomethyl)phenyl)thiophene-2-yl) |
| 35 | Ms-D-Ser(Bn) | $CH_2CH_2NHSO_2$(5-(3-(bis(2-methoxyethyl)aminomethyl)phenyl)thiophene-2-yl) |
| 36 | Ms-D-Ser(Bn) | $CH_2CH_2NHSO_2$(5-(3-cyanophenyl)thiophene-2-yl) |
| 37 | Ms-D-Ser(Bn) | $CH_2CH_2NHSO_2$(5-(3-(thiomorpholinoCH$_2$)phenyl)thiophene-2-yl) |
| 38 | Ms-D-Ser(Bn) | $CH_2CH_2NHSO_2$(5-(3-(4-ketopiperidinylCH$_2$)phenyl)thiophene-2-yl) |
| 39 | Ms-L-Ser(Bn). | $CH_2CH_2NHSO_2Ph$ |

* * * * *

UNITED STATES PATENT AND TRADEMARK OFFICE
CERTIFICATE OF CORRECTION

PATENT NO.     : 6,288,231 B1
DATED          : September 11, 2001
INVENTOR(S)    : Sankar Chatterjee et al.

It is certified that error appears in the above-identified patent and that said Letters Patent is hereby corrected as shown below:

Title page,
Item [56], References Cited, OTHER PUBLICATIONS,
"Bihovsky et al.," reference, please insert -- acids -- after "amino" and before "as".
"*Remington's Pharmaceutical Sciences*," reference, please delete "Mark" and insert -- Mack -- therefor.

Column 1,
Line 9, please delete "is a".
Line 24, please delete "proteasell" and insert -- protease -- therefor.

Column 2,
Line 35, please delete "G–B–(CHR$^4$),"  and insert -- G–B–(CHR$^4$)$_v$ -- therefor.

Column 3,
Line 17, please delete "(CH$_2$)pNH-L" and insert -- (CH$_2$)$_p$NH-L -- therefor.
Line 38, please delete "RI" and insert -- R$^1$ -- therefor.
Line 42, please delete "OS0$_2$" and insert -- OSO$_2$- -- therefor.

Column 4,
Line 32, please delete "SO$_2$N(R$^8$)R$^{10}$I" and insert -- SO$_2$N(R$^8$)R$^{10}$ -- therefor.
Line 46, please delete "–S(=C)$_2$R$^8$" and insert -- –S(=O)$_2$R$^8$ -- therefor.

Column 6,
Line 18, please delete "hetercalkyl" and insert -- heteroalkyl -- therefor.
Line 55, please delete "S(=C)$_2$R$^6$" and insert -- S(=O)$_2$R$^6$ -- thereof --.
Line 66, please delete "S(=)$_2$R$^7$" and insert -- S(=O)$_2$R$^7$ -- thereof --.

Column 7,
Line 5, please delete "OS0$_2$-aryl" and insert -- OSO$_2$-aryl -- therefor.

Column 8,
Line 6, please delete "a-amino" and insert -- α-amino -- therefor.
Line 58, please delete "C, N, or S)" and insert -- O, N, or S) -- therefor.

Column 9,
Line 5, please delete "at Least" and insert -- at least -- therefor.
Line 6, please delete "atomn" and insert -- atom -- therefor.
Line 29, please delete "a-amino" and insert -- α-amino -- therefor.

UNITED STATES PATENT AND TRADEMARK OFFICE
CERTIFICATE OF CORRECTION

PATENT NO.    : 6,288,231 B1
DATED         : September 11, 2001
INVENTOR(S)   : Sankar Chatterjee et al.

It is certified that error appears in the above-identified patent and that said Letters Patent is hereby corrected as shown below:

Column 18,
Line 63, please delete "Rf" and insert -- $R_f$ -- therefor.

Column 19,
Line 43, please delete "135 IC" and insert -- $135^\circ$ C -- therefor.

Column 20,
Line 55, please delete "8-mercaptoethanol" and insert -- β-mercaptoethanol -- therefor.

Column 22,
Line 8, please delete "E inhibition" and insert -- % inhibition -- therefor.

Column 42,
Line 57, please delete "$CH_2CH_2NHSO_2$(5-pyrid-2-ylthiophene-2-yl)," and insert
-- $CH_2CH_2NHSO_2$(5-pyrid-2-ylthiophene-2-yl), -- therefor.

Column 43,
Line 26, please delete "$CH_2CH_2NHSQ_2$(5-(3-(4-ketopiperidinylCH $_2$)phenyl" and
insert -- $CH_2CH_2NHSO_2$(5-(3-(4-ketopiperidinyl$CH_2$)phenyl) -- therefor.

Signed and Sealed this

Twelfth Day of October, 2004

JON W. DUDAS
*Director of the United States Patent and Trademark Office*